United States Patent [19]

Takeshiba et al.

[11] Patent Number: 5,773,618
[45] Date of Patent: Jun. 30, 1998

[54] TRICYCLIC COMPOUNDS HAVING FUNGICIDAL ACTIVITY, THEIR PREPARATION AND THEIR USE

[75] Inventors: Hideo Takeshiba, Kusatsu; Chiaki Imai; Hiroshi Ohta, both of Shiga-ken; Shigehiro Kato, Ohmihachiman; Hiroyuki Itoh, Moriyama, all of Japan

[73] Assignee: Sankyo Company, Limited, Tokyo, Japan

[21] Appl. No.: 855,915

[22] Filed: May 14, 1997

[30] Foreign Application Priority Data

May 15, 1996 [JP] Japan ..................................... 8-120301
Mar. 4, 1997 [JP] Japan ..................................... 9-048828

[51] Int. Cl.⁶ ........................ C07D 221/04; C07D 209/04
[52] U.S. Cl. ............................... 546/98; 546/98; 546/111; 548/510
[58] Field of Search ....................................... 546/98, 111

[56] References Cited

U.S. PATENT DOCUMENTS 3,917,838 11/1975 Bass et al. .

FOREIGN PATENT DOCUMENTS 0 657 427 6/1995 European Pat. Off. .
607864 7/1994 Japan ........................... C07D 471/06

OTHER PUBLICATIONS

Bass et al, "Tricyclic Amides: A New Class of Systemic Fungicides Active against Rice Blast Disease", Journal of Agricultural and Food Chemistry, vol. 29, No. 3, 1981 pp. 576–579.

Patent Abstracts of Japan, vol. 8, No. 255 (C–253), 21 Nov. 1984 of JP 59 134792 A (Nippon Kayaku KK), 2 Aug. 1984.
Database WPI, Week 8006, Derwent Publications Ltd., London, GB; AN 80–10337C of JP 54 163 813 A (Kumiai Chem. Ind. Co. Ltd.), 26 Dec. 1979.
Burke et al, "Biomimetic Syntheses of the Bisindole Alkaloids Villalstonine and Alstonisidine", Journal of The American Chemical Society, vol. 95, No. 2, 1973, pp. 546–552.
Sheinkman et al, "Dialkylaminoacetylindoles—a new group of local anesthetics", KHIM.–Farm. ZH., vol. 11, No. 6, 1977, pp. 59–64.
Franke et al, "1.7–Zyklisierung von Acetoacetyl–indolen", Archiv Der Pharmazie, vol. 309, No. 3, 1976, pp. 185–189.

*Primary Examiner*—Johann Richter
*Assistant Examiner*—Joseph Murray
*Attorney, Agent, or Firm*—Frishauf, Holtz, Goodman, Langer & Chick, P.C.

[57] ABSTRACT

Compounds of formula (I):

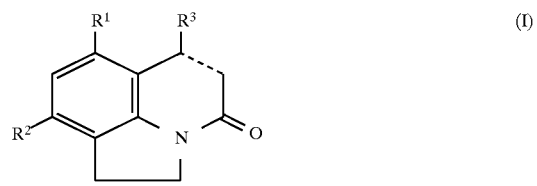

[wherein: $R^1$ represents halogen, alkyl, haloalkyl, alkoxy, haloalkoxy, cycloalkyl, or cycloalkyloxy; $R^2$ represents hydrogen or halogen; $R^3$ represents hydrogen, alkyl, or cycloalkyl; and the dotted line represents a single or double carbon—carbon bond]; and salts thereof have valuable fungicidal activities which make them of considerable value in agriculture and horticulture.

48 Claims, No Drawings

TRICYCLIC COMPOUNDS HAVING FUNGICIDAL ACTIVITY, THEIR PREPARATION AND THEIR USE

BACKGROUND TO THE INVENTION

The present invention relates to a series of new pyrroloquinoline derivatives which have valuable fungicidal activities which make them of considerable value in agriculture and horticulture. It also provides methods and compositions using the compounds of the present invention as well as processes for their preparation.

The compounds of the present invention have the following basic molecular structure:

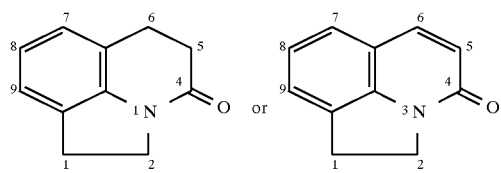

Certain compounds having a similar structure are known and are described in Japanese Patent Publication (Kokoku) No. Sho 52-48176 (equivalent to U.S. Pat. Nos. 3,917,838 and 4,008,325), J. Agric. Food Chem., Vol. 29, No. 3, 576–579 (1981) and Japanese Unexamined Patent Publication (Kokai) No. Sho 54-163813.

The compounds of the present invention are characterised by a substituent at the 7-position of the above-mentioned basic structure.

Japanese Unexamined Patent Publication (Kokai) No. Sho 54-163813 discloses the compound of formula:

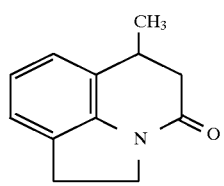

that is, with a methyl group at the 6-position and no substituent at the 7-position.

Although the disclosures of certain of the other prior art embraces the compounds of the present invention, as well as a class of superficially similar but unrelated compounds having a carbonyl group at the 2-position instead of the 4-position, there is no disclosure of the limited class of compounds claimed herein.

When compounds having fungicidal activities are used in practice as agricultural chemicals, it is generally considered highly desirable that they should be capable of exhibiting their activities when used in relatively small amounts. It is also necessary that they should be free from phytotoxicity. Further, in recent years, labor-saving has become of greater importance in the treatment of crops and greater emphasis has been put on the safety of workers. For these purposes, compounds having systemic (osmosis migration) characteristics are particularly advantageous.

We have now surprisingly discovered that a limited series of compounds having the above-mentioned basic structure and having a substituent at the 7-position have excellent fungicidal activity for use in agriculture and horticulture, and have good systemic (osmosis migration) characteristics without any phytotoxicity, unlike the prior art compounds referred to above.

BRIEF SUMMARY OF THE INVENTION

It is therefore an object of the present invention to provide a series of new pyrroloquinoline compounds.

It is a further, and more specific object of the present invention to provide such compounds which are useful for the treatment and prevention of fungal infections in plants and which may be used in agriculture and horticulture.

Other objects and advantages will become apparent as the description proceeds.

The compounds of the present invention are those compounds of formula (I):

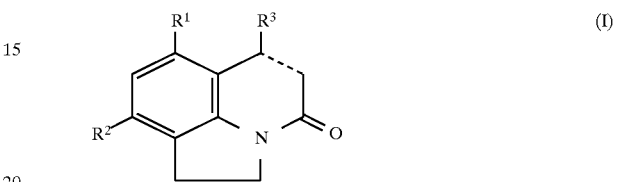

wherein:
$R^1$ represents
  a halogen atom,
  an alkyl group having from 1 to 6 carbon atoms,
  a haloalkyl group having from 1 to 6 carbon atoms,
  an alkoxy group having from 1 to 6 carbon atoms,
  a haloalkoxy group having from 1 to 6 carbon atoms,
  a cycloalkyl group having from 3 to 7 carbon atoms, or
  a cycloalkyloxy group having from 3 to 7 carbon atoms;
$R^2$ represents a hydrogen atom or a halogen atom;
$R^3$ represents
  a hydrogen atom,
  an alkyl group having from 1 to 6 carbon atoms, or
  a cycloalkyl group having from 3 to 7 carbon atoms; and
the dotted line represents a single or double carbon—carbon bond;
and salts thereof.

Other compounds of the present invention are those compounds of formula (II), which are intermediates in the preparation of the compounds of formula (I):

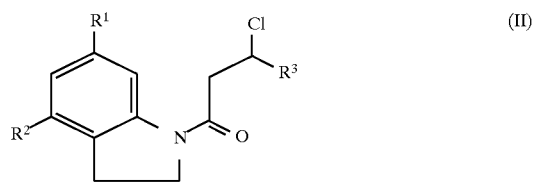

wherein $R^1$, $R^2$ and $R^3$ are as defined above.

Further compounds of the present invention are those compounds of formula (III), which are intermediates in the preparation of the compounds of formula (I):

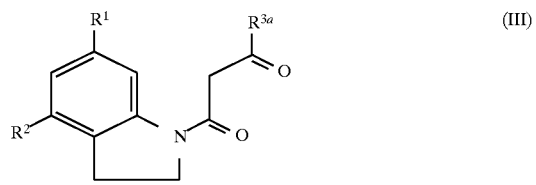

wherein $R^1$ and $R^2$ are as defined above, and $R^{3a}$ represents an alkyl group having from 1 to 6 carbon atoms.

Further compounds of the present invention are those compounds of formula (IV), which are intermediates in the preparation of the compounds of formula (I):

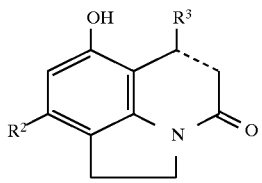

wherein $R^2$, $R^3$ and the dotted line are as defined above.

The invention also provides processes for preparing the compounds of the present invention, which are described in greater detail hereafter. In particular, one process for preparing compounds of formula (I) in which $R^1$ represents a fluorine atom, that is compounds of formula (If):

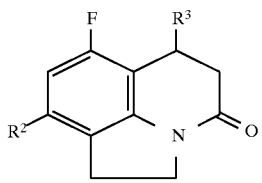

wherein $R^2$ and $R^3$ are as defined above, comprises the steps: diazotising a compound of formula (V):

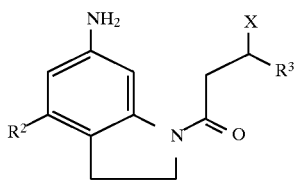

wherein X represents a chlorine or bromine atom and $R^2$ and $R^3$ are as defined above, in the presence of a fluorine-containing compound capable of generating a fluorine anion, and heating the product to give a compound of formula (VI):

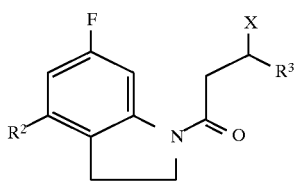

wherein X, $R^2$ and $R^3$ are as defined above, and then ring-closing said compound of formula (VI) to give said compound of formula (If).

The present invention still further provides a method of protecting plants from fungal infection by applying to said plants, to reproductive matter of said plants or to a locus including said plants an effective mount of at least one compound of formula (I) or a salt thereof.

The present invention still further provides a method of treating fungal infection in a plant applying to said plant or to a locus including said plant an effective mount of at least one compound of formula (I) or a salt thereof.

DETAILED DESCRIPTION OF THE INVENTION

In the compounds of the present invention, where $R^1$ or $R^2$ represents a halogen atom, this may be a fluorine, chlorine, bromine or iodine atom. In the case of $R^1$, this is preferably a fluorine, chlorine or bromine atom, more preferably a fluorine or chlorine atom. In the case of $R^2$, this is preferably a fluorine, chlorine or bromine atom, more preferably a fluorine or chlorine atom, and most preferably a fluorine atom.

Where $R^1$ or $R^3$ represents an alkyl group, this may be straight or branched chain alkyl group having from 1 to 6 carbon atoms, and examples include the methyl, ethyl, propyl, isopropyl, butyl, isobutyl, sec-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups. More preferred groups are those straight or branched chain alkyl groups having from 1 to 4 carbon atoms, still more preferably the methyl or ethyl groups, and most preferably the methyl group.

Where $R^1$ represents an alkoxy group, this may be a straight or branched chain alkoxy group having from 1 to 6 carbon atoms, and examples include the methoxy, ethoxy, propoxy, isopropoxy, butoxy, isobutoxy, sec-butoxy, t-butoxy, pentyloxy, isopentyloxy, 2-methylbutoxy, neopentyloxy, 1-ethylpropoxy, hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy and 2-ethylbutoxy groups. More preferred groups are those straight or branched chain alkoxy groups having from 1 to 4 carbon atoms, still more preferably the methoxy or ethoxy groups, and most preferably the methoxy group.

Where $R^1$ represents a haloalkyl group, this may be a straight or branched chain alkyl group having from 1 to 6 carbon atoms which is substituted by at least one, and preferably from 1 to 3, halogen atoms. The halogen atom may be a fluorine, chlorine, bromine or iodine atom, preferably a fluorine or chlorine atom, and more preferably a fluorine atom. Where there is more than one halogen atom, the atoms may be the same as or different from each other. The alkyl group may be any of those alkyl groups exemplified above in relation to $R^1$. Specific examples of such haloalkyl groups include the trifluoromethyl, trichloromethyl, difluorobromomethyl, difluorochloromethyl, difluoromethyl, dichloromethyl, dibromomethyl, fluoromethyl, chloromethyl, bromomethyl, iodomethyl, 2,2,2-trichloroethyl, 2,2,2-trifluoroethyl, 2-bromoethyl, 2-chloroethyl, 2-fluoroethyl, 2,2-dibromoethyl, 3-chloropropyl, 3,3,3-trifluoropropyl, 4-fluorobutyl, 5,5,5-trichloropentyl and 6,6,6-trifluorohexyl groups. More preferred haloalkyl groups are those straight or branched chain haloalkyl groups having from 1 to 3 carbon atoms and having from 1 to 3 of the same halogen atoms. Still more preferred are those groups in which a methyl group or an ethyl group is substituted with from 1 to 3 fluorine atoms or chlorine atoms, most preferably a trifluoromethyl group or a difluoromethyl group.

Where $R^1$ represents a haloalkoxy group, this may be a straight or branched chain alkoxy group having from 1 to 6 carbon atoms which is substituted by at least one, and preferably from 1 to 3, halogen atoms. The halogen atom may be a fluorine, chlorine, bromine or iodine atom, preferably a fluorine or chlorine atom, and more preferably a fluorine atom. Where there is more than one halogen atom, the atoms may be the same as or different from each other. The alkoxy group may be any of those alkoxy groups exemplified above in relation to $R^1$. Specific examples of such haloalkoxy groups include the trifluoromethoxy, trichloromethoxy, difluorobromomethoxy, difluorochloromethoxy, difluoromethoxy, dichloromethoxy, dibromomethoxy, fluoromethoxy, chloromethoxy, bromomethoxy, iodomethoxy, 2,2,2-trichloroethoxy, 2,2,2- trifluoroethoxy, 2-bromoethoxy, 2-chloroethoxy, 2-fluoroethoxy, 2,2-dibromoethoxy, 3-chloropropoxy, 3,3,3-trifluoropropoxy, 4-fluorobutoxy, 5,5,5-trichloropentyloxy and 6,6,6-trifluorohexyloxy groups. More preferred haloalkoxy groups are those straight or branched chain haloalkoxy groups having from 1 to 3 carbon atoms and having from 1 to 3 of the same halogen atoms. Still more preferred are those groups in which a methoxy group or an ethoxy group is substituted with 1 to 3 fluorine atoms or chlorine atoms, most preferably a trifluoromethoxy group or a difluoromethoxy group.

Where $R^1$ or $R^3$ represents a cycloalkyl group, this has from 3 to 7, more preferably 5 or 6, ring carbon atoms, and examples include the cyclopropyl, cyclobutyl, cyclopentyl, cyclohexyl and cycloheptyl groups, of which the cyclopentyl and cyclohexyl groups are preferred.

Where $R^1$ represents a cycloalkyloxy group, this has from 3 to 7, more preferably 5 or 6, ring carbon atoms, and examples include the cyclopropyloxy, cyclobutyloxy, cyclopentyloxy, cyclohexyloxy and cycloheptyloxy groups, of which the cyclopentyloxy and cyclohexyloxy groups are preferred.

The compounds of the present invention can form acid addition salts. Examples of such acid addition salts include: salts with mineral acids, especially hydrohalic acids (such as hydrofluoric acid, hydrobromic acid, hydroiodic acid or hydrochloric acid), nitric acid, perchloric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; and salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid.

The compounds of the present invention can also form solvates, especially hydrates, and such solvates, especially hydrates, are also included in the present invention.

In the compounds of the present invention, $R^1$ preferably represents a fluorine atom, a chlorine atom, a bromine atom, an alkyl group having from 1 to 6 carbon atoms, a haloalkyl group having from 1 to 6 carbon atoms and having from 1 to 3 halogen atoms which may be the same as or different from each other, an alkoxy group having from 1 to 6 carbon atoms or a haloalkoxy group having from 1 to 6 carbon atoms and having from 1 to 3 halogen atoms which may be the same as or different from each other. More preferably, $R^1$ represents a fluorine atom, a chlorine atom, a methyl group, a methoxy group, a difluoromethoxy group or a trifluoromethoxy group, still more preferably a fluorine atom, a chlorine atom, a methyl group or a difluoromethoxy group, even more preferably a fluorine atom, a chlorine atom or a difluoromethoxy group, and most preferably a fluorine atom or a chlorine atom.

In the compounds of the present invention, $R^2$ preferably represents a hydrogen atom, a fluorine atom, a chlorine atom or a bromine atom, more preferably a hydrogen atom, a fluorine atom or a chlorine atom, still more preferably a hydrogen atom or a fluorine atom, and most preferably a hydrogen atom.

In the compounds of the present invention, $R^3$ preferably represents a hydrogen atom or an alkyl group having from 1 to 4 carbon atoms, more preferably a hydrogen atom, a methyl group or an ethyl group, still more preferably a hydrogen atom or a methyl group, and most preferably a hydrogen atom in the case where the dotted line is a single bond and a methyl group in the case where the dotted line is a double bond.

Preferred classes of compounds of the present invention are those compounds of formula (I) and salts thereof in which:
(1A) $R^1$ represents a fluorine atom, a chlorine atom, a bromine atom, an alkyl group having from 1 to 6 carbon atoms, a haloalkyl group having from 1 to 6 carbon atoms and having from 1 to 3 halogen atoms which may be the same as or different from each other, an alkoxy group having from 1 to 6 carbon atoms or a haloalkoxy group having from 1 to 6 carbon atoms and having from 1 to 3 halogen atoms which may be the same as or different from each other.
(1B) $R^3$ represents a hydrogen atom or an alkyl group having from 1 to 4 carbon atoms.

Particularly preferred compounds are those compounds of formula (I) and salts thereof in which $R^1$ is as defined in (1A) and $R^3$ is as defined in (1B) above.

More preferred classes of compounds of the present invention are those compounds of formula (I) and salts thereof in which:
(2A) $R^1$ represents a fluorine atom, a chlorine atom, a methyl group, a methoxy group, a difluoromethoxy group or a trifluoromethoxy group.
(2B) $R^2$ represents a hydrogen atom, a fluorine atom, a chlorine atom or a bromine atom.
(2C) $R^3$ represents a hydrogen atom, a methyl group or an ethyl group.

Particularly preferred compounds are those compounds of formula (I) and salts thereof in which $R^1$ is as defined in (2A), $R^2$ is as defined in (2B), and $R^3$ is as defined in (2C) above.

Still more preferred classes of compounds of the present invention are those compounds of formula (I) and salts thereof in which:
(3A) $R^1$ represents a fluorine atom, a chlorine atom, a methyl group or a difluoromethoxy group.
(3B) $R^2$ represents a hydrogen atom, a fluorine atom or a chlorine atom.
(3C) $R^3$ represents a hydrogen atom.
(3D) The dotted line represents a single bond.

Particularly preferred compounds are those compounds of formula (I) and salts thereof in which $R^1$ is as defined in (3A), $R^2$ is as defined in (3B), $R^3$ is as defined in (3C), and the dotted line is as defined in (3D) above.

Alternative more preferred classes of compounds of the present invention are those compounds of formula (I) and salts thereof in which:
(4A) $R^2$ represents a hydrogen atom, a fluorine atom, a chlorine atom or a difluoromethoxy group.
(4B) $R^3$ represents a methyl group.
(4C) The dotted line represents a double bond.

Particularly preferred compounds are those compounds of formula (I) and salts thereof in which $R^1$ is as defined in (3A), $R^2$ is as defined in (4A), $R^3$ is as defined in (4B), and the dotted line is as defined in (4C) above.

Still more preferred classes of compounds of the present invention are those compounds of formula (I) and salts thereof in which:
(5A) $R^1$ represents a fluorine atom, a chlorine atom or a difluoromethoxy group.
(5B) $R^2$ represents a hydrogen atom or a fluorine atom.

Particularly preferred compounds are those compounds of formula (I) and salts thereof in which $R^1$ is as defined in (5A), $R^2$ is as defined in (5B), $R^3$ is as defined in (3C), and the dotted line is as defined in (3D) above.

The most preferred classes of compounds of the present invention are those compounds of formula (I) and salts thereof in which:

(6A) $R^1$ represents a fluorine atom or a chlorine atom.

(6B) $R^2$ represents a hydrogen atom.

Particularly preferred compounds are those compounds of formula (I) and salts thereof in which $R^1$ is as defined in (6A), $R^2$ is as defined in (6B), $R^3$ is as defined in (3C), and the dotted line is as defined in (3D) above.

Specific examples of compounds of the present invention are those tetrahydro-4H-pyrrolo[3,2,1-ij]quinolin-4-one compounds of formula (Ia) and those dihydro-4H-pyrrolo[3,2,1-ij]quinolin-4-one compounds of formula (Ib). The meaning of the various substituent groups shown in these formulae are given in the corresponding one of Tables 1 and 2. That is Table 1 relates to formula (Ia) and Table 2 relates to formula (Ib). Specific examples of intermediate compounds employed in the present invention are those compounds of formulae (II), (III) and (IV), in which the meaning of the various substituent groups shown in these formulae are given in Tables 3, 4 and 5, respectively.

In the Tables, the following abbreviations are used:

| | |
|---|---|
| cHx | cyclohexyl; |
| cPn | cyclopentyl. |

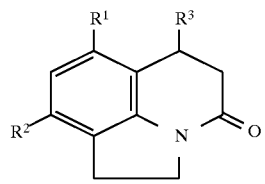
(Ia)

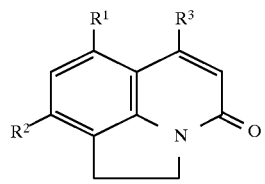
(Ib)

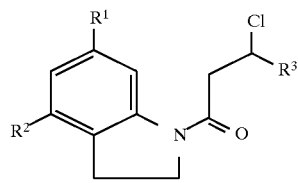
(II)

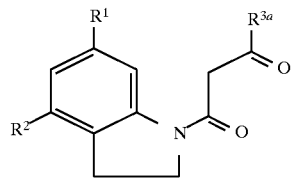
(III)

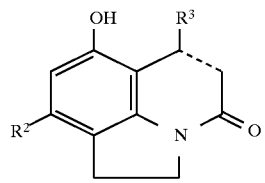
(IV)

TABLE 1

| Cpd.No. | $R^1$ | $R^2$ | $R^3$ |
|---|---|---|---|
| 1 | F | H | H |
| 2 | Cl | H | H |
| 3 | Br | H | H |
| 4 | I | H | H |
| 5 | $CH_3$ | H | H |
| 6 | $CH_2CH_3$ | H | H |
| 7 | $CH_2CH_2CH_3$ | H | H |
| 8 | $CH(CH_3)_2$ | H | H |
| 9 | $(CH_2)_3CH_3$ | H | H |
| 10 | $CH(CH_3)CH_2CH_3$ | H | H |
| 11 | $CH_2CH(CH_3)_2$ | H | H |
| 12 | $C(CH_3)_3$ | H | H |
| 13 | $(CH_2)_4CH_3$ | H | H |
| 14 | cPn | H | H |
| 15 | $(CH_2)_5CH_3$ | H | H |
| 16 | cHx | H | H |
| 17 | $OCH_3$ | H | H |
| 18 | $OCH_2CH_3$ | H | H |
| 19 | $OCH_2CH_2CH_3$ | H | H |
| 20 | $OCH(CH_3)_2$ | H | H |
| 21 | $O(CH_2)_3CH_3$ | H | H |
| 22 | $OCH(CH_3)CH_2CH_3$ | H | H |
| 23 | $OCH_2CH(CH_3)_2$ | H | H |
| 24 | $OC(CH_3)_3$ | H | H |
| 25 | $O(CH_2)_4CH_3$ | H | H |
| 26 | O-cPn | H | H |
| 27 | $O(CH_2)_5CH_3$ | H | H |
| 28 | O-cHx | H | H |
| 29 | $CF_3$ | H | H |
| 30 | $CF_2Br$ | H | H |
| 31 | $CF_2Cl$ | H | H |
| 32 | $CHF_2$ | H | H |
| 33 | $CH_2F$ | H | H |
| 34 | $OCF_3$ | H | H |
| 35 | $OCF_2Br$ | H | H |
| 36 | $OCF_2Cl$ | H | H |
| 37 | $OCHF_2$ | H | H |
| 38 | $OCH_2F$ | H | H |
| 39 | F | F | H |
| 40 | Cl | F | H |
| 41 | F | Cl | H |
| 42 | Cl | Cl | H |
| 43 | $CH_3$ | F | H |
| 44 | $CH_3$ | Cl | H |
| 45 | $OCH_3$ | F | H |
| 46 | $OCH_3$ | Cl | H |
| 47 | $OCH_2CH_3$ | F | H |
| 48 | $OCH_2CH_3$ | Cl | H |
| 49 | $OCHF_2$ | F | H |
| 50 | $OCHF_2$ | Cl | H |
| 51 | $OCH_2F$ | F | H |
| 52 | $OCH_2F$ | Cl | H |
| 53 | F | H | $CH_3$ |
| 54 | Cl | H | $CH_3$ |
| 55 | Br | H | $CH_3$ |
| 56 | I | H | $CH_3$ |
| 57 | $CH_3$ | H | $CH_3$ |
| 58 | $CH_2CH_3$ | H | $CH_3$ |
| 59 | $CH_2CH_2CH_3$ | H | $CH_3$ |
| 60 | $CH(CH_3)_2$ | H | $CH_3$ |
| 61 | $(CH_2)_3CH_3$ | H | $CH_3$ |
| 62 | $CH(CH_3)CH_2CH_3$ | H | $CH_3$ |
| 63 | $CH_2CH(CH_3)_2$ | H | $CH_3$ |
| 64 | $C(CH_3)_3$ | H | $CH_3$ |
| 65 | $(CH_2)_4CH_3$ | H | $CH_3$ |
| 66 | cPn | H | $CH_3$ |
| 67 | $(CH_2)_5CH_3$ | H | $CH_3$ |
| 68 | cHx | H | $CH_3$ |
| 69 | $OCH_3$ | H | $CH_3$ |
| 70 | $OCH_2CH_3$ | H | $CH_3$ |
| 71 | $OCH_2CH_2CH_3$ | H | $CH_3$ |
| 72 | $OCH(CH_3)_2$ | H | $CH_3$ |
| 73 | $O(CH_2)_3CH_3$ | H | $CH_3$ |
| 74 | $OCH(CH_3)CH_2CH_3$ | H | $CH_3$ |
| 75 | $OCH_2CH(CH_3)_2$ | H | $CH_3$ |
| 76 | $OC(CH_3)_3$ | H | $CH_3$ |
| 77 | $O(CH_2)_4CH_3$ | H | $CH_3$ |

TABLE 1-continued

| Cpd.No. | $R^1$ | $R^2$ | $R^3$ |
|---|---|---|---|
| 78 | O-cPn | H | $CH_3$ |
| 79 | $O(CH_2)_5CH_3$ | H | $CH_3$ |
| 80 | O-cHx | H | $CH_3$ |
| 81 | $CF_3$ | H | $CH_3$ |
| 82 | $CF_2Br$ | H | $CH_3$ |
| 83 | $CF_2Cl$ | H | $CH_3$ |
| 84 | $CHF_2$ | H | $CH_3$ |
| 85 | $CH_2F$ | H | $CH_3$ |
| 86 | $OCF_3$ | H | $CH_3$ |
| 87 | $OCF_2Br$ | H | $CH_3$ |
| 88 | $OCF_2Cl$ | H | $CH_3$ |
| 89 | $OCHF_2$ | H | $CH_3$ |
| 90 | $OCH_2F$ | H | $CH_3$ |
| 91 | F | F | $CH_3$ |
| 92 | Cl | F | $CH_3$ |
| 93 | F | Cl | $CH_3$ |
| 94 | Cl | Cl | $CH_3$ |
| 95 | $CH_3$ | F | $CH_3$ |
| 96 | $CH_3$ | Cl | $CH_3$ |
| 97 | $OCH_3$ | F | $CH_3$ |
| 98 | $OCH_3$ | Cl | $CH_3$ |
| 99 | $OCH_2CH_3$ | F | $CH_3$ |
| 100 | $OCH_2CH_3$ | Cl | $CH_3$ |
| 101 | $OCHF_2$ | F | $CH_3$ |
| 102 | $OCHF_2$ | Cl | $CH_3$ |
| 103 | $OCH_2F$ | F | $CH_3$ |
| 104 | $OCH_2F$ | Cl | $CH_3$ |
| 105 | F | H | $CH_2CH_3$ |
| 106 | Cl | H | $CH_2CH_2CH_3$ |
| 107 | F | F | $CH(CH_3)_2$ |
| 108 | Cl | Cl | $(CH_2)_3CH_3$ |
| 109 | $OCH_3$ | H | $CH(CH_3)CH_2CH_3$ |
| 110 | $OCHF_2$ | H | $CH_2CH(CH_3)_2$ |
| 111 | $OCHF_2$ | H | $C(CH_3)_3$ |
| 112 | F | H | $(CH_2)_4CH_3$ |
| 113 | Cl | H | cPn |
| 114 | F | F | $(CH_2)_5CH_3$ |
| 115 | Cl | Cl | cHx |
| 116 | F | Br | H |
| 117 | Cl | Br | H |
| 118 | $OCHF_2$ | Br | H |
| 119 | F | I | H |
| 120 | Cl | I | H |
| 121 | $OCHF_2$ | I | H |

TABLE 2

| Cpd.No. | $R^1$ | $R^2$ | $R^3$ |
|---|---|---|---|
| 201 | F | H | H |
| 202 | Cl | H | H |
| 203 | Br | H | H |
| 204 | I | H | H |
| 205 | $CH_3$ | H | H |
| 206 | $CH_2CH_3$ | H | H |
| 207 | $CH_2CH_2CH_3$ | H | H |
| 208 | $CH(CH_3)_2$ | H | H |
| 209 | $(CH_2)_3CH_3$ | H | H |
| 210 | $CH(CH_3)CH_2CH_3$ | H | H |
| 211 | $CH_2CH(CH_3)_2$ | H | H |
| 212 | $C(CH_3)_3$ | H | H |
| 213 | $(CH_2)_4CH_3$ | H | H |
| 214 | cPn | H | H |
| 215 | $(CH_2)_5CH_3$ | H | H |
| 216 | cHx | H | H |
| 217 | $OCH_3$ | H | H |
| 218 | $OCH_2CH_3$ | H | H |
| 219 | $OCH_2CH_2CH_3$ | H | H |
| 220 | $OCH(CH_3)_2$ | H | H |
| 221 | $O(CH_2)_3CH_3$ | H | H |
| 222 | $OCH(CH_3)CH_2CH_3$ | H | H |
| 223 | $OCH_2CH(CH_3)_2$ | H | H |
| 224 | $OC(CH_3)_3$ | H | H |
| 225 | $O(CH_2)_4CH_3$ | H | H |

TABLE 2-continued

| Cpd.No. | $R^1$ | $R^2$ | $R^3$ |
|---|---|---|---|
| 226 | O-cPn | H | H |
| 227 | $O(CH_2)_5CH_3$ | H | H |
| 228 | O-cHx | H | H |
| 229 | $CF_3$ | H | H |
| 230 | $CF_2Br$ | H | H |
| 231 | $CF_2Cl$ | H | H |
| 232 | $CHF_2$ | H | H |
| 233 | $CH_2F$ | H | H |
| 234 | $OCF_3$ | H | H |
| 235 | $OCF_2Br$ | H | H |
| 236 | $OCF_2Cl$ | H | H |
| 237 | $OCHF_2$ | H | H |
| 238 | $OCH_2F$ | H | H |
| 239 | F | F | H |
| 240 | Cl | F | H |
| 241 | F | Cl | H |
| 242 | Cl | Cl | H |
| 243 | $CH_3$ | F | H |
| 244 | $CH_3$ | Cl | H |
| 245 | $OCH_3$ | F | H |
| 246 | $OCH_3$ | Cl | H |
| 247 | $OCH_2CH_3$ | F | H |
| 248 | $OCH_2CH_3$ | Cl | H |
| 249 | $OCHF_2$ | F | H |
| 250 | $OCHF_2$ | Cl | H |
| 251 | $OCH_2F$ | F | H |
| 252 | $OCH_2F$ | Cl | H |
| 253 | F | H | $CH_3$ |
| 254 | Cl | H | $CH_3$ |
| 255 | Br | H | $CH_3$ |
| 256 | I | H | $CH_3$ |
| 257 | $CH_3$ | H | $CH_3$ |
| 258 | $CH_2CH_3$ | H | $CH_3$ |
| 259 | $CH_2CH_2CH_3$ | H | $CH_3$ |
| 260 | $CH(CH_3)_2$ | H | $CH_3$ |
| 261 | $(CH_2)_3CH_3$ | H | $CH_3$ |
| 262 | $CH(CH_3)CH_2CH_3$ | H | $CH_3$ |
| 263 | $CH_2CH(CH_3)_2$ | H | $CH_3$ |
| 264 | $C(CH_3)_3$ | H | $CH_3$ |
| 265 | $(CH_2)_4CH_3$ | H | $CH_3$ |
| 266 | cPn | H | $CH_3$ |
| 267 | $(CH_2)_5CH_3$ | H | $CH_3$ |
| 268 | cHx | H | $CH_3$ |
| 269 | $OCH_3$ | H | $CH_3$ |
| 270 | $OCH_2CH_3$ | H | $CH_3$ |
| 271 | $OCH_2CH_2CH_3$ | H | $CH_3$ |
| 272 | $OCH(CH_3)_2$ | H | $CH_3$ |
| 273 | $O(CH_2)_3CH_3$ | H | $CH_3$ |
| 274 | $OCH(CH_3)CH_2CH_3$ | H | $CH_3$ |
| 275 | $OCH_2CH(CH_3)_2$ | H | $CH_3$ |
| 276 | $OC(CH_3)_3$ | H | $CH_3$ |
| 277 | $O(CH_2)_4CH_3$ | H | $CH_3$ |
| 278 | O-cPn | H | $CH_3$ |
| 279 | $O(CH_2)_5CH_3$ | H | $CH_3$ |
| 280 | O-cHx | H | $CH_3$ |
| 281 | $CF_3$ | H | $CH_3$ |
| 282 | $CF_2Br$ | H | $CH_3$ |
| 283 | $CF_2Cl$ | H | $CH_3$ |
| 284 | $CHF_2$ | H | $CH_3$ |
| 285 | $CH_2F$ | H | $CH_3$ |
| 286 | $OCF_3$ | H | $CH_3$ |
| 287 | $OCF_2Br$ | H | $CH_3$ |
| 288 | $OCF_2Cl$ | H | $CH_3$ |
| 289 | $OCHF_2$ | H | $CH_3$ |
| 290 | $OCH_2F$ | H | $CH_3$ |
| 291 | F | F | $CH_3$ |
| 292 | Cl | F | $CH_3$ |
| 293 | F | Cl | $CH_3$ |
| 294 | Cl | Cl | $CH_3$ |
| 295 | $CH_3$ | F | $CH_3$ |
| 296 | $CH_3$ | Cl | $CH_3$ |
| 297 | $OCH_3$ | F | $CH_3$ |
| 298 | $OCH_3$ | Cl | $CH_3$ |
| 299 | $OCH_2CH_3$ | F | $CH_3$ |
| 300 | $OCH_2CH_3$ | Cl | $CH_3$ |
| 301 | $OCHF_2$ | F | $CH_3$ |
| 302 | $OCHF_2$ | Cl | $CH_3$ |

TABLE 2-continued

| Cpd.No. | $R^1$ | $R^2$ | $R^3$ |
|---|---|---|---|
| 303 | $OCH_2F$ | F | $CH_3$ |
| 304 | $OCH_2F$ | Cl | $CH_3$ |
| 305 | F | H | $CH_2CH_3$ |
| 306 | Cl | H | $CH_2CH_2CH_3$ |
| 307 | F | F | $CH(CH_3)_2$ |
| 308 | Cl | Cl | $(CH_2)_3CH_3$ |
| 309 | $OCH_3$ | H | $CH(CH_3)CH_2CH_3$ |
| 310 | $OCHF_2$ | H | $CH_2CH(CH_3)_2$ |
| 311 | $OCHF_2$ | H | $C(CH_3)_3$ |
| 312 | F | H | $(CH_2)_4CH_3$ |
| 313 | Cl | H | cPn |
| 314 | F | F | $(CH_2)_5CH_3$ |
| 315 | Cl | Cl | cHx |
| 316 | F | Br | $CH_3$ |
| 317 | Cl | Br | $CH_3$ |
| 318 | $OCHF_2$ | Br | $CH_3$ |
| 319 | F | I | $CH_3$ |
| 320 | Cl | I | $CH_3$ |
| 321 | $OCHF_2$ | I | $CH_3$ |

TABLE 3

| Cpd. No. | $R^1$ | $R^2$ | $R^3$ |
|---|---|---|---|
| 401 | F | H | H |
| 402 | Cl | H | H |
| 403 | Br | H | H |
| 404 | I | H | H |
| 405 | $CH_3$ | H | H |
| 406 | $CH_2CH_3$ | H | H |
| 407 | $CH_2CH_2CH_3$ | H | H |
| 408 | $CH(CH_3)_2$ | H | H |
| 409 | $(CH_2)_3CH_3$ | H | H |
| 410 | $CH(CH_3)CH_2CH_3$ | H | H |
| 411 | $CH_2CH(CH_3)_2$ | H | H |
| 412 | $C(CH_3)_3$ | H | H |
| 413 | $(CH_2)_4CH_3$ | H | H |
| 414 | cPn | H | H |
| 415 | $(CH_2)_5CH_3$ | H | H |
| 416 | cHx | H | H |
| 417 | $OCH_3$ | H | H |
| 418 | $OCH_2CH_3$ | H | H |
| 419 | $OCH_2CH_2CH_3$ | H | H |
| 420 | $OCH(CH_3)_2$ | H | H |
| 421 | $O(CH_2)_3CH_3$ | H | H |
| 422 | $OCH(CH_3)CH_2CH_3$ | H | H |
| 423 | $OCH_2CH(CH_3)_2$ | H | H |
| 424 | $OC(CH_3)_3$ | H | H |
| 425 | $O(CH_2)_4CH_3$ | H | H |
| 426 | O-cPn | H | H |
| 427 | $O(CH_2)_5CH_3$ | H | H |
| 428 | O-cHx | H | H |
| 429 | $CF_3$ | H | H |
| 430 | $CF_2Br$ | H | H |
| 431 | $CF_2Cl$ | H | H |
| 432 | $CHF_2$ | H | H |
| 433 | $CH_2F$ | H | H |
| 434 | $OCF_3$ | H | H |
| 435 | $OCF_2Br$ | H | H |
| 436 | $OCF_2Cl$ | H | H |
| 437 | $OCHF_2$ | H | H |
| 438 | $OCH_2F$ | H | H |
| 439 | F | F | H |
| 440 | Cl | F | H |
| 441 | F | Cl | H |
| 442 | Cl | Cl | H |
| 443 | $CH_3$ | F | H |
| 444 | $CH_3$ | Cl | H |
| 445 | $OCH_3$ | F | H |
| 446 | $OCH_3$ | Cl | H |
| 447 | $OCH_2CH_3$ | F | H |
| 448 | $OCH_2CH$ | Cl | H |
| 449 | $OCHF_2$ | F | H |
| 450 | $OCHF_2$ | Cl | H |

TABLE 3-continued

| Cpd. No. | $R^1$ | $R^2$ | $R^3$ |
|---|---|---|---|
| 451 | $OCH_2F$ | F | H |
| 452 | $OCH_2F$ | Cl | H |
| 453 | F | H | $CH_3$ |
| 454 | Cl | H | $CH_3$ |
| 455 | Br | H | $CH_3$ |
| 456 | I | H | $CH_3$ |
| 457 | $CH_3$ | H | $CH_3$ |
| 458 | $CH_2CH_3$ | H | $CH_3$ |
| 459 | $CH_2CH_2CH_3$ | H | $CH_3$ |
| 460 | $CH(CH_3)_2$ | H | $CH_3$ |
| 461 | $(CH_2)_3CH_3$ | H | $CH_3$ |
| 462 | $CH(CH_3)CH_2CH_3$ | H | $CH_3$ |
| 463 | $CH_2CH(CH_3)_2$ | H | $CH_3$ |
| 464 | $C(CH_3)_3$ | H | $CH_3$ |
| 465 | $(CH_2)_4CH_3$ | H | $CH_3$ |
| 466 | cPn | H | $CH_3$ |
| 467 | $(CH_2)_5CH_3$ | H | $CH_3$ |
| 468 | cHx | H | $CH_3$ |
| 469 | $OCH_3$ | H | $CH_3$ |
| 470 | $OCH_2CH_3$ | H | $CH_3$ |
| 471 | $OCH_2CH_2CH_3$ | H | $CH_3$ |
| 472 | $OCH(CH_3)_2$ | H | $CH_3$ |
| 473 | $O(CH_2)_3CH_3$ | H | $CH_3$ |
| 474 | $OCH(CH_3)CH_2CH_3$ | H | $CH_3$ |
| 475 | $OCH_2CH(CH_3)_2$ | H | $CH_3$ |
| 476 | $OC(CH_3)_3$ | H | $CH_3$ |
| 477 | $O(CH_2)_4CH_3$ | H | $CH_3$ |
| 478 | O-cPn | H | $CH_3$ |
| 479 | $O(CH_2)_5CH_3$ | H | $CH_3$ |
| 480 | O-cHx | H | $CH_3$ |
| 481 | $CF_3$ | H | $CH_3$ |
| 482 | $CF_2Br$ | H | $CH_3$ |
| 483 | $CF_2Cl$ | H | $CH_3$ |
| 484 | $CHF_2$ | H | $CH_3$ |
| 485 | $CH_2F$ | H | $CH_3$ |
| 486 | $OCF_3$ | H | $CH_3$ |
| 487 | $OCF_2Br$ | H | $CH_3$ |
| 488 | $OCF_2Cl$ | H | $CH_3$ |
| 489 | $OCHF_2$ | H | $CH_3$ |
| 490 | $OCH_2F$ | H | $CH_3$ |
| 491 | F | F | $CH_3$ |
| 492 | Cl | F | $CH_3$ |
| 493 | F | Cl | $CH_3$ |
| 494 | Cl | Cl | $CH_3$ |
| 495 | $CH_3$ | F | $CH_3$ |
| 496 | $CH_3$ | Cl | $CH_3$ |
| 497 | $OCH_3$ | F | $CH_3$ |
| 498 | $OCH_3$ | Cl | $CH_3$ |
| 499 | $OCH_2CH_3$ | F | $CH_3$ |
| 500 | $OCH_2CH_3$ | Cl | $CH_3$ |
| 501 | $OCHF_2$ | F | $CH_3$ |
| 502 | $OCHF_2$ | Cl | $CH_3$ |
| 503 | $OCH_2F$ | F | $CH_3$ |
| 504 | $OCH_2F$ | Cl | $CH_3$ |
| 505 | F | H | $CH_2CH_3$ |
| 506 | Cl | H | $CH_2CH_2CH_3$ |
| 507 | F | F | $CH(CH_3)_2$ |
| 508 | Cl | Cl | $(CH_2)_3CH_3$ |
| 509 | $OCH_3$ | H | $CH(CH_3)CH_2CH_3$ |
| 510 | $OCHF_2$ | H | $CH_2CH(CH_3)_2$ |
| 511 | $OCHF_2$ | H | $C(CH_3)_3$ |
| 512 | F | H | $(CH_2)_4CH_3$ |
| 513 | Cl | H | cPn |
| 514 | F | F | $(CH_2)_5CH_3$ |
| 515 | Cl | Cl | cHx |
| 516 | F | Br | H |
| 517 | Cl | Br | H |
| 518 | $OCHF_2$ | Br | H |
| 519 | F | I | H |
| 520 | Cl | I | H |
| 521 | $OCHF_2$ | I | H |
| 522 | F | Br | $CH_3$ |
| 523 | Cl | Br | $CH_3$ |
| 524 | $OCHF_2$ | Br | $CH_3$ |

TABLE 3-continued

| Cpd. No. | R$^1$ | R$^2$ | R$^3$ |
|---|---|---|---|
| 525 | F | I | CH$_3$ |
| 526 | Cl | I | CH$_3$ |
| 527 | OCHF$_2$ | I | CH$_3$ |

TABLE 4

| Cpd. No. | R$^1$ | R$^2$ | R$^{3a}$ |
|---|---|---|---|
| 601 | F | H | CH$_3$ |
| 602 | Cl | H | CH$_3$ |
| 603 | Br | H | CH$_3$ |
| 604 | I | H | CH$_3$ |
| 605 | CH$_3$ | H | CH$_3$ |
| 606 | CH$_2$CH$_3$ | H | CH$_3$ |
| 607 | CH$_2$CH$_2$CH$_3$ | H | CH$_3$ |
| 608 | CH(CH$_3$)$_2$ | H | CH$_3$ |
| 609 | (CH$_2$)$_3$CH$_3$ | H | CH$_3$ |
| 610 | CH(CH$_3$)CH$_2$CH$_3$ | H | CH$_3$ |
| 611 | CH$_2$CH(CH$_3$)$_2$ | H | CH$_3$ |
| 612 | C(CH$_3$)$_3$ | H | CH$_3$ |
| 613 | (CH$_2$)$_4$CH$_3$ | H | CH$_3$ |
| 614 | cPn | H | CH$_3$ |
| 615 | (CH$_2$)$_5$CH$_3$ | H | CH$_3$ |
| 616 | cHx | H | CH$_3$ |
| 617 | OCH$_3$ | H | CH$_3$ |
| 618 | OCH$_2$CH$_3$ | H | CH$_3$ |
| 619 | OCH$_2$CH$_2$CH$_3$ | H | CH$_3$ |
| 620 | OCH(CH$_3$)$_2$ | H | CH$_3$ |
| 621 | O(CH$_2$)$_3$CH$_3$ | H | CH$_3$ |
| 622 | OCH(CH$_3$)CH$_2$CH$_3$ | H | CH$_3$ |
| 623 | OCH$_2$CH(CH$_3$)$_2$ | H | CH$_3$ |
| 624 | OC(CH$_3$)$_3$ | H | CH$_3$ |
| 625 | O(CH$_2$)$_4$CH$_3$ | H | CH$_3$ |
| 626 | O-cPn | H | CH$_3$ |
| 627 | O(CH$_2$)$_5$CH$_3$ | H | CH$_3$ |
| 628 | O-cHx | H | CH$_3$ |
| 629 | CF$_3$ | H | CH$_3$ |
| 630 | CF$_2$Br | H | CH$_3$ |
| 631 | CF$_2$Cl | H | CH$_3$ |
| 632 | CHF$_2$ | H | CH$_3$ |
| 633 | CH$_2$F | H | CH$_3$ |
| 634 | OCF$_3$ | H | CH$_3$ |
| 635 | OCF$_2$Br | H | CH$_3$ |
| 636 | OCF$_2$Cl | H | CH$_3$ |
| 637 | OCHF$_2$ | H | CH$_3$ |
| 638 | OCH$_2$F | H | CH$_3$ |
| 639 | F | F | CH$_3$ |
| 640 | Cl | F | CH$_3$ |
| 641 | F | Cl | CH$_3$ |
| 642 | Cl | Cl | CH$_3$ |
| 643 | CH$_3$ | F | CH$_3$ |
| 644 | CH$_3$ | Cl | CH$_3$ |
| 645 | OCH$_3$ | F | CH$_3$ |
| 646 | OCH$_3$ | Cl | CH$_3$ |
| 647 | OCH$_2$CH$_3$ | F | CH$_3$ |
| 648 | OCH$_2$CH$_3$ | Cl | CH$_3$ |
| 649 | OCHF$_2$ | F | CH$_3$ |
| 650 | OCHF$_2$ | Cl | CH$_3$ |
| 651 | OCH$_2$F | F | CH$_3$ |
| 652 | OCH$_2$F | Cl | CH$_3$ |
| 653 | F | H | CH$_2$CH$_3$ |
| 654 | Cl | H | CH$_2$CH$_2$CH$_3$ |
| 655 | F | F | CH(CH$_3$)$_2$ |
| 656 | Cl | Cl | (CH$_2$)$_3$CH$_3$ |
| 657 | OCH$_3$ | H | CH(CH$_3$)CH$_2$CH$_3$ |
| 658 | OCHF$_2$ | H | CH$_2$CH(CH$_3$)$_2$ |
| 659 | OCHF$_2$ | H | C(CH$_3$)$_3$ |
| 660 | F | H | (CH$_2$)$_4$CH$_3$ |
| 661 | Cl | H | cPn |
| 662 | F | F | (CH$_2$)$_5$CH$_3$ |
| 663 | Cl | Cl | cHx |
| 664 | F | Br | CH$_3$ |
| 665 | Cl | Br | CH$_3$ |
| 666 | OCHF$_2$ | Br | CH$_3$ |

TABLE 4-continued

| Cpd. No. | R$^1$ | R$^2$ | R$^{3a}$ |
|---|---|---|---|
| 667 | F | I | CH$_3$ |
| 668 | Cl | I | CH$_3$ |
| 669 | OCHF$_2$ | I | CH$_3$ |

TABLE 5

| Cpd. No | R$^2$ | R$^3$ | dotted line |
|---|---|---|---|
| 701 | H | H | Single bond |
| 702 | F | H | Single bond |
| 703 | Cl | H | single bond |
| 704 | H | CH$_3$ | Single bond |
| 705 | F | CH$_3$ | single bond |
| 706 | Cl | CH$_3$ | Single bond |
| 707 | H | CH$_2$CH$_3$ | Single bond |
| 708 | H | CH$_2$CH$_2$CH$_3$ | Single bond |
| 709 | F | CH(CH$_3$)$_2$ | Single bond |
| 710 | Cl | (CH$_2$)$_3$CH$_3$ | Single bond |
| 711 | H | CH(CH$_3$)CH$_2$CH$_3$ | Single bond |
| 712 | H | CH$_2$CH(CH$_3$)$_2$ | Single bond |
| 713 | H | C(CH$_3$)$_3$ | Single bond |
| 714 | H | (CH$_2$)$_4$CH$_3$ | Single bond |
| 715 | H | cPn | Single bond |
| 716 | F | (CH$_2$)$_5$CH$_3$ | Single bond |
| 717 | Cl | cHx | single bond |
| 718 | Br | H | Single bond |
| 719 | I | H | Single bond |
| 720 | Br | CH$_3$ | Single bond |
| 721 | I | CH$_3$ | Single bond |
| 751 | H | H | Double bond |
| 752 | F | H | Double bond |
| 753 | Cl | H | Double bond |
| 754 | H | CH$_3$ | Double bond |
| 755 | F | CH$_3$ | Double bond |
| 756 | Cl | CH$_3$ | Double bond |
| 757 | H | CH$_2$CH$_3$ | Double bond |
| 758 | H | CH$_2$CH$_2$CH$_3$ | Double bond |
| 759 | F | CH(CH$_3$)$_2$ | Double bond |
| 760 | Cl | (CH$_2$)$_3$CH$_3$ | Double bond |
| 761 | H | CH(CH$_3$)CH$_2$CH$_3$ | Double bond |
| 762 | H | CH$_2$CH(CH$_3$)$_2$ | Double bond |
| 763 | H | C(CH$_3$)$_3$ | Double bond |
| 764 | H | (CH$_2$)$_4$CH$_3$ | Double bond |
| 765 | H | cPn | Double bond |
| 766 | F | (CH$_2$)$_5$CH$_3$ | Double bond |
| 767 | Cl | cHx | Double bond |
| 768 | Br | H | Double bond |
| 769 | I | H | Double bond |
| 770 | Br | CH$_3$ | Double bond |
| 771 | I | CH$_3$ | Double bond |

Of the compounds of formula (Ia) and (Ib) listed above, the following are particularly preferred, that is Compounds No. 1, 2, 5, 17, 37, 39, 269 and 289. Of these, the preferred compounds are Compounds No. 1, 2, 5, 37, 39 and 289. The most preferred compounds are Compounds No.:

1. 7-Fluoro-1,2,5,6-tetrahydro-4H-pyrrolo[3,2,1-ij] quinolin-4-one;
2. 7-Chloro-1,2,5,6-tetrahydro-4H-pyrrolo[3,2,1-ij] quinolin-4-one;
39. 7,9-Difluoro-1,2,5,6-tetrahydro-4H-pyrrolo[3,2,1-ij] quinolin-4-one; and
289. 7-Difluoromethoxy-6-methyl-1,2-dihydro-4H-pyrrolo [3,2,1-ij]quinolin-4-one;
and salts thereof.

The compounds of the present invention may be prepared by a variety of methods well known in the art for the preparation of compounds of this type, for example as illustrated in the following Methods A to G.

Method A

Compounds of formula (I) in which R$^1$ represents a halogen atom, an alkyl group having from 1 to 6 carbon atoms, a haloalkyl group having from 1 to 6 carbon atoms or a cycloalkyl group having from 3 to 7 carbon atoms and the dotted line represents a single bond, that is compounds of formula (Ia-1) may be prepared as shown in the following Reaction Scheme A:

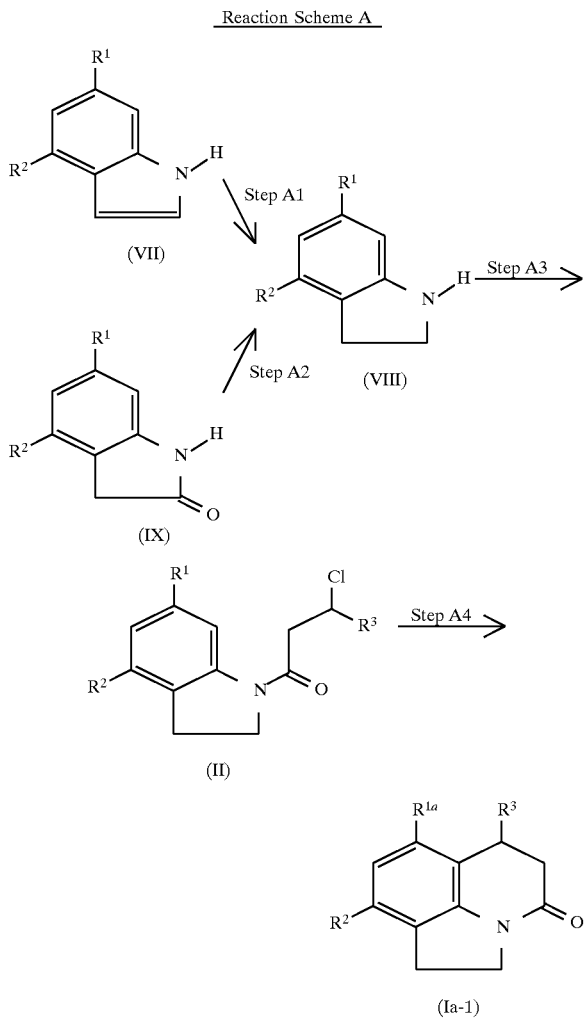

In the above formulae, $R^1$, $R^2$ and $R^3$ are as defined above and $R^{1a}$ represents a halogen atom, an alkyl group having from 1 to 6 carbon atoms, a haloalkyl group having from 1 to 6 carbon atoms or a cycloalkyl group having from 3 to 7 carbon atoms.

Step A1

In this Step, an indoline compound of formula (VIII) is prepared by reducing an indole compound of formula (VII).

The reduction can be carried out by the method of Gordon W. Gribble et al . described in Synthesis, 859 (1977), the disclosures of which are incorporated herein by reference.

Step A2

In this Step, an indoline compound of formula (VIII) is prepared by reducing an oxindole compound of formula (IX).

The compound of formula (IX), which is the starting material in the present step can be prepared, for example, by the method described in Synthesis, 51 (1993).

There is no particular restriction on the nature of the reducing agents used, and any reducing agent commonly used in reactions of this type, that is the reduction of an amide to an amine, may equally be used here. Examples of such reducing agents include: lithium aluminum hydride, alane, and diborane. Of these, we prefer diborane.

The amount of the reducing agent used is preferably from 1 to 10 equivalents per equivalent of the compound of formula (IX), more preferably from 2 to 3 equivalents.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include ethers, such as diethyl ether, diisopropyl ether or tetrahydrofuran. Of these, we prefer tetrahydrofuran.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −50° C. to the boiling point of the solvent employed, more preferably from room temperature to the boiling point of the solvent. The time required for the reaction may also vary widely, depending on many factors, notably the reaction temperature and the nature of the reagents and solvent employed. However, provided that the reaction is effected under the preferred conditions outlined above, a period of from 1 hour to 4 days, more preferably from 4 hours to 3 days, will usually suffice.

After completion of the reaction, the reaction mixture may be subjected to post-treatment in the same manner as in a conventional reduction reaction. For example, since the compound of formula (VIII) is converted to a complex with the reducing agent or the reaction product of the reducing agent upon completion of the reaction, the complex is first decomposed with an acid, and the mixture is then neutralised with a base to obtain the compound of formula (VIII).

There is no particular restriction on the nature of the acids used, and any acid commonly used in reactions of this type may equally be used here. Examples of such acids include: protonic acids, such as hydrochloric acid, sulfuric acid, nitric acid, and phosphoric acid; and organic carboxylic acids. Of these, we prefer hydrochloric acid.

There is likewise no particular restriction on the nature of the bases used for neutralisation, and any base commonly used in reactions of this type may equally be used here. Examples of such bases include: hydroxides, such as sodium hydroxide or potassium hydroxide; carbonates, such as sodium carbonate or potassium carbonate; and hydrogencarbonates, such as sodium hydrogencarbonate or potassium hydrogencarbonate.

Step A3

In this Step, a compound of formula (II) is prepared by reacting a chlorine-substituted acid chloride of formula: $ClCH(R^3)CH_2COCl$ (wherein $R^3$ is as defined above) with the indoline compound of formula (VIII) in the presence or absence of a base.

The amount of the compound of formula: $ClCH(R^3)CH_2COCl$ used in this step is preferably from 1 to 3 equivalents, more preferably from 1 to 1.5 equivalents, per equivalent of the compound of formula (VIII).

The presence of a base is not essential in the present step. If a base is employed, there is no particular restriction on the nature of the bases used, and any base commonly used in reactions of this type may equally be used here. Examples of such bases include: alkali metal carbonates, such as sodium carbonate or potassium carbonate; alkali metal hydrogencarbonates, such as sodium hydrogencarbonate or potassium hydrogencarbonate; alkali metal hydrides, such as sodium hydride, lithium hydride or potassium hydride; alkali metal hydroxides, such as sodium hydroxide or potassium hydroxide; alkaline earth metal hydroxides, such as barium hydroxide; alkali metal alkoxides, such as sodium methoxide, sodium ethoxide or potassium t-butoxide; organic bases, such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo [5.4.0]undec-7-ene (DBU); and organometallic bases, such as butyllithium or lithium diisopropylamide. Of these, we prefer triethylamine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as hexane, cyclohexane, benzene or toluene; halogenated hydrocarbons, such as methylene chloride, dichloroethane, chloroform or tetrachloroethane; ethers, such as dioxane, diethyl ether, tetrahydrofuran (THF) or ethylene glycol dimethyl ether; amides, such as dimethylformamide, dimethylacetamide or hexamethylphosphoric triamide (HMPA); ketones, such as acetone, methyl ethyl ketone, methyl isobutyl ketone or cyclohexanone; nitriles, such as acetonitrile or isobutyronitrile; and esters, such as methyl acetate, ethyl acetate or propyl acetate. Of these, we prefer acetone.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 150° C., more preferably from 10° C. to 90° C. The time required for the reaction may also vary widely, depending on many factors, notably the reaction temperature and the nature of the reagents and solvent employed, as well as upon whether or not a base is employed. However, provided that the reaction is effected under the preferred conditions outlined above, a period of from 10 minutes to 24 hours, more preferably from 30 minutes to 10 hours, will usually suffice.

Step A4

In this Step, a compound of the present invention of formula (Ia-1) is prepared by carrying out a ring closure of a compound of formula (IIa), which is a compound of formula (II) in which $R^1$ represents a halogen atom, an alkyl group having from 1 to 6 carbon atoms, a haloalkyl group having from 1 to 6 carbon atoms or a cycloalkyl group having from 3 to 7 carbon atoms. This is carried out under the reaction condition generally known as a Friedel-Crafts reaction. It may also be carried out by the procedures described in Japanese Patent Publication (Kokoku) No. Sho 52-48176.

The reaction is carried out in the presence of Lewis acid. There is no particular restriction on the nature of the Lewis acids used, and any Lewis acid commonly used in Friedel-Crafts reactions of this type may equally be used here. Examples of such Lewis acids include: aluminum chloride, iron trichloride, tin dichloride, tin tetrachloride, boron tribromide, boron trichloride, boron trifluoride, zinc chloride, zinc bromide, titanium trichloride, titanium tetrachloride and mixtures of any two or more thereof. Of these, we prefer aluminum chloride or tin tetrachloride, most preferably aluminum chloride.

The amount of Lewis acid used in the present step is preferably from 1 to 10 equivalents per equivalent of the compound of formula (IIa). A more preferred amount is from 1 to 5 equivalents, most preferably from 2 to 3 equivalents.

The presence of a solvent is not essential in this Step. If used, there is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride, dichloroethane, tetrachloroethane, dichlorohexane or dichlorooctane; hydrocarbons, such as hexane, cyclohexane, octane, decane or dodecane; and aromatic solvents, such as nitrobenzene, dichlorotoluene or mesitylene.

The reaction can take place over a wide range of temperatures, and the precise reaction temperature is not critical to the invention. The preferred reaction temperature will depend upon such factors as the presence or absence of the solvent and the nature of the solvent, and the starting material or reagent used. However, in general, we find it convenient to carry out the reaction at a temperature of from room temperature to 200° C., more preferably from 80° C. to 180° C., and still more preferably from 120° C. to 160° C. The time required for the reaction may also vary widely, depending on many factors, notably the reaction temperature, the presence or absence of the solvent and the nature of the reagents and solvent employed. However, provided that the reaction is effected under the preferred conditions outlined above, a period of from 30 minutes to 24 hours, more preferably from 1 hour to 4 hours, will usually suffice.

After completion of the reaction, the reaction mixture may be subjected to post-treatment in the same manner as in a conventional Friedel-Crafts reaction. For example, the reaction mixture is poured into ice-water or ice-water containing dilute hydrochloric acid or ice-water or ice-water containing dilute hydrochloric acid is poured to the reaction mixture, and then the mixture is extracted with an appropriate organic solvent.

Method B

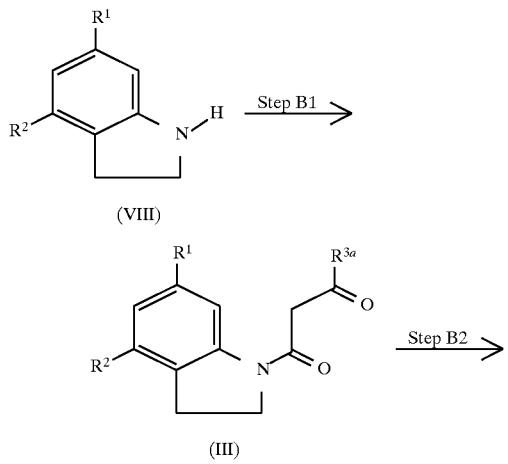

-continued
Reaction Scheme B

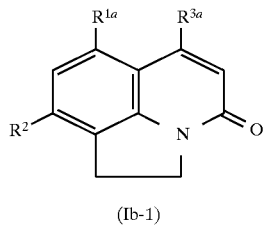

(Ib-1)

In the above formulae, $R^1$, $R^{1a}$ and $R^2$ are as defined above and $R^{3a}$ represents an alkyl group having from 1 to 6 carbon atoms or a cycloalkyl group having from 3 to 7 carbon atoms.

Step B1

In this Step, a compound of formula (III) is prepared by reacting the indoline compound of formula (VIII) with (a) a diketene (a ketene dimer) or (b) an ester compound of formula: $R^{3a}COCH_2COOR$ [wherein $R^{3a}$ is as defined above and R represents an alkyl group].

Step B1(a)

In this Step, only those compounds of formula (IIIa) in which $R^{3a}$ represents a methyl group are prepared.

The reaction of the indoline compound of formula (VIII) with the diketene is carried out in the presence of a solvent.

The amount of diketene used in the present step is preferably from 1 to 10 equivalents, preferably from 1 to 3 equivalents, per equivalent of the compound of formula (VIII).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform, carbon tetrachloride, dichloroethane, chlorobenzene or dichlorobenzene; ethers, such as diethyl ether, diisopropyl ether, tetrahydrofuran, dioxane, dimethoxyethane or diethylene glycol dimethyl ether; nitriles, such as acetonitrile or isobutyronitrile; amides, such as formamide, dimethylformamide, dimethylacetamide, hexamethylphosphoric triamide and 1,3-dimethyl-2-imidazolidinone; sulfoxides, such as dimethyl sulfoxide; and sulfones, such as sulfolane. Of these, we prefer halogenated hydrocarbons, such as methylene chloride or dichloroethane.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10° C. to 100° C., more preferably from 20° C. to 80° C. The time required for the reaction may also vary widely, depending on many factors, notably the reaction temperature and the nature of the reagents and solvent employed. However, provided that the reaction is effected under the preferred conditions outlined above, a period of from 1 hour to 10 hours, more preferably from 2 hours to 4 hours, will usually suffice.

Step B1(b)

This step is carried out in the presence or absence of a base and in the presence of a solvent.

There is no particular restriction on the nature of the bases used, and any base commonly used in reactions of this type may equally be used here. Examples of such bases include: alkali metal carbonates, such as sodium carbonate or potassium carbonate; alkali metal hydrogencarbonates, such as sodium hydrogencarbonate or potassium hydrogencarbonate; an alkali metal hydrides, such as sodium hydride, lithium hydride and potassium hydride; alkali metal hydroxides, such as sodium hydroxide or potassium hydroxide; alkaline earth metal hydroxides, such as barium hydroxide; alkali metal alkoxides, such as sodium methoxide, sodium ethoxide or potassium t-butoxide; organic bases, such as triethylamine, tributylamine, diisopropylethylamine, N-methylmorpholine, pyridine, 4-(N,N-dimethylamino)-pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU); and organometallic bases, such as butyllithium or lithium diisopropylamide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform, carbon tetrachloride, dichloroethane, chlorobenzene or dichlorobenzene; ethers, such as diethyl ether, diisopropyl ether, tetrahydrofuran, dioxane, dimethoxyethane or diethylene glycol dimethyl ether; nitriles, such as acetonitrile or isobutyronitrile; amides, such as formamide, dimethylformamide, dimethylacetamide, hexamethylphosphoric triamide or 1,3-dimethyl-2-imidazolidinone; sulfoxides, such as dimethyl sulfoxide; and sulfones, such as sulfolane.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10° C. to 150° C., more preferably from 20° C. to 100° C. The time required for the reaction may also vary widely, depending on many factors, notably the reaction temperature and the nature of the reagents and solvent employed. However, provided that the reaction is effected under the preferred conditions outlined above, a period of from 1 hour to 24 hours, more preferably from 2 hours to 14 hours, will usually suffice.

Step B2

In this Step, a compound of the present invention of formula (Ib-1) [that is a compound of formula (I) in which $R^3$ represents an alkyl group having from 1 to 6 carbon atoms or a cycloalkyl group having from 3 to 7 carbon atoms and the dotted line represents a double bond] is prepared by treating the compound of formula (III) with a dehydrating agent to cause ring closure.

There is no particular restriction on the nature of the dehydrating agents used, and any dehydrating agent commonly used in reactions of this type may equally be used here. Examples of such dehydrating agents include acids, such as concentrated sulfuric acid and polyphosphoric acid.

The presence of a solvent is not essential in this Step. If used, there is no particular restriction on the nature of the solvent to be employed, provided that it has no adverse effect on the reaction or on the reagents involved and that it can dissolve the reagents, at least to some extent. Examples of suitable solvents include: hydrocarbons, such as pentane, hexane, cyclohexane, octane, decane, dodecane, toluene and xylene; halogenated hydrocarbons, such as methylene chloride, dichloroethane, tetrachloroethane, chlorobenzene and dichlorobenzene; and ethers, such as diethyl ether, diiospropyl ether, tetrahydrofuran, dioxane, dimethoxyethane, and diethylene glycol dimethyl ether.

The reaction can take place over a wide range of temperatures, and the precise reaction temperature is not critical to the invention. The preferred reaction temperature will depend upon such factors as the presence or absence of the solvent and the nature of the solvent, and the starting material or reagent used. However, in general, we find it convenient to carry out the reaction at a temperature of from 30° C. to 150° C., more preferably from 50° C. to 120° C. The time required for the reaction may also vary widely, depending on many factors, notably the reaction temperature, the presence or absence of the solvent and the nature of the reagents and solvent employed. However, provided that the reaction is effected under the preferred conditions outlined above, a period of from 1 hour to 6 hours, more preferably from 10 minutes to 2 hours, will usually suffice.

Method C

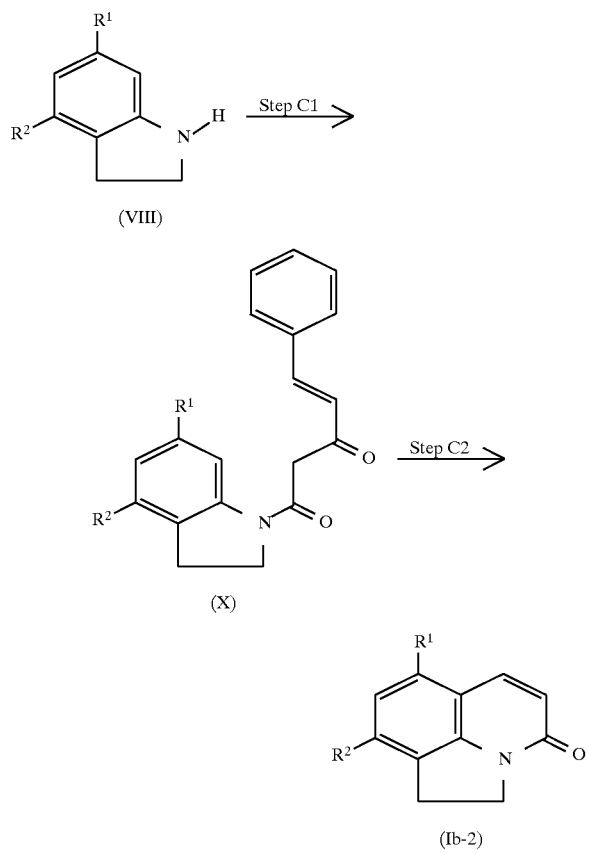

In the above formulae, $R^1$ and $R^2$ are as defined above.

Step C1

In this Step, a compound of formula (X) is prepared by reacting the indoline compound of formula (VIII) as a starting material with cinnamoyl chloride.

This step can be carried out, for example, by the method described in J. Agric. Food Chem. Vol. 29, No. 3, 576–579 (1981), the disclosures of which are incorporated herein by reference.

Step C2

In this Step, the compound of the present invention of formula (Ib-2) [that is a compound of formula (I) in which $R^3$ represents a hydrogen atom and the dotted line represents a double bond] is prepared by heating the compound (X) in the presence of anhydrous aluminum chloride.

The present step, as in Step C1, can also be carried out by the method described in J. Agric. Food Chem., Vol. 29, No. 3, 576–579 (1981).

Method D

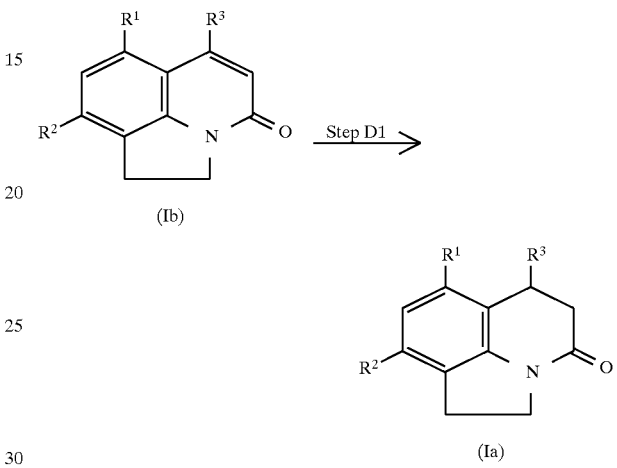

In the above formulae, $R^1$, $R^2$ and $R^3$ are as defined above.

Step D1

In this Step, the compound of the present invention of formula (Ia) is prepared by catalytically reducing the compound of formula (Ib) which is also a compound of the present invention.

The reaction may be carried out by a conventional catalytic reduction method using hydrogen gas in the presence of a solvent and a catalyst.

The reaction is carried out under a hydrogen atmosphere, in which case, the gas pressure is preferably from 1 to 20 atmospheres, more preferably from 1 to 6 atmospheres.

There is no particular restriction on the nature of the catalysts used, and any catalyst commonly used in catalytic reduction may equally be used here. Examples of such catalysts include a palladium-on-carbon catalyst or a platinum catalyst having a 5% to 10% by weight content of the active metal.

The catalyst is usually used in an amount of from 1/300 to 1/10 equivalent, preferably 1/200 to 1/30 equivalent, per equivalent of the compound of formula (Ib).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include alcohols, such as methanol, ethanol or propanol.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 10° C. to 80° C., more preferably from 20° C. to 50° C. The time required for the reaction may also vary widely, depending on many factors, notably the reaction temperature and the nature of the reagents and solvent employed. However, provided that the reaction is effected under the preferred conditions outlined above, a period of from 1 hour to 6 hours, more preferably from 1 hour to 2 hours, will usually suffice.

Method E

Reaction Scheme E

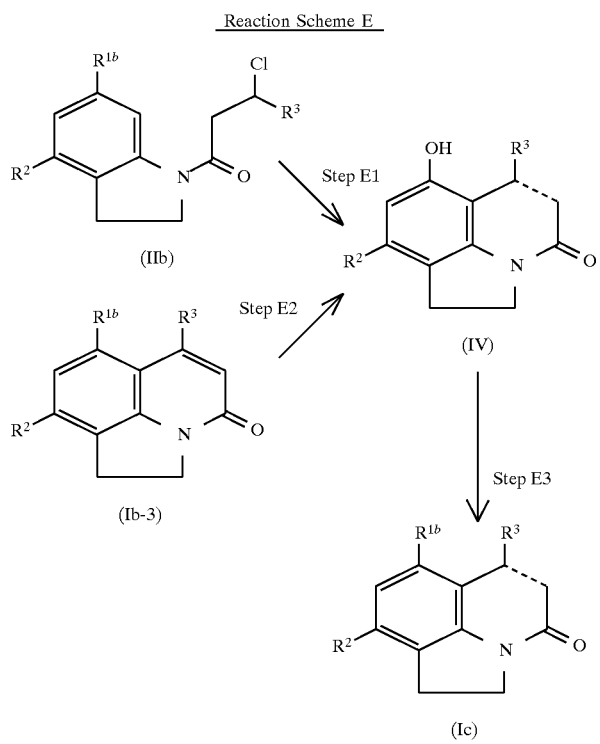

In the above formulae:

$R^2$, $R^3$ and the dotted line are as defined above; and $R^{1b}$ represents an alkoxy group having from 1 to 6 carbon atoms, a haloalkoxy group having from 1 to 6 carbon atoms or a cycloalkyloxy group having from 3 to 7 carbon atoms.

Step E1

In this Step, a compound of formula (IVa) is prepared. This is a compound in which the 7-position of the pyrrolo [3,2,1-ij]quinoline ring is a hydroxy group and corresponds to a compound of formula (IV) in which the dotted line is a single bond. The starting material is a compound of formula (IIb), which corresponds to a compound of formula (II), in which $R^1$ represents an alkoxy group having from 1 to 6 carbon atoms, a haloalkoxy group having from 1 to 6 carbon atoms or a cycloalkyloxy group having from 3 to 7 carbon atoms.

This step can be carried out in the same manner as in Step A4. When the reaction is carried out under the ring closure conditions described in Step A4, the alkoxy, haloalkoxy or cycloalkyloxy group is converted into a hydroxy group at the same time when the ring closure is carried out.

Step E2

In this Step, a compound of formula (IVb) is prepared. This is a compound in which the 7-position of the pyrrolo [3,2,1-ij]quinoline ring is a hydroxy group and corresponds to a compound of formula (IV) in which the dotted line is a double bond. The starting material is a compound of formula (Ib-3). The compound of formula (Ib-3) is a compound of formula (Ib), in which $R^1$ represents an alkoxy group having from 1 to 6 carbon atoms, a haloalkoxy group having from 1 to 6 carbon atoms or a cycloalkyloxy group having from 3 to 7 carbon atoms.

This step can be carried out by the conventional methods described in "Protective Groups in Organic Synthesis" [Second Edition, John Wiley and Sons, Inc. (1991)] edited by Greene Wuts et al. the disclosures of which are incorporated herein by reference, for example, by treatment with a Lewis acid such as boron tribromide.

Step E3

In this Step, a compound of the present invention of formula (Ic) [which is a compound of formula (I) in which $R^1$ represents an alkoxy group having from 1 to 6 carbon atoms, a haloalkoxy group having from 1 to 6 carbon atoms or a cycloalkyloxy group having from 3 to 7 carbon atoms] is prepared by converting the hydroxy group at the 7-position of the compound of formula (IV) into an alkoxy or haloalkoxy group having from 1 to 6 carbon atoms or a cycloalkyloxy group having from 3 to 7 carbon atoms.

This step is carried out by alkylation with an alkylating agent or by cycloalkylation with a cycloalkylating agent in the presence of a base.

There is no particular restriction on the nature of the alkylating agents used, and any alkylating agent commonly used in reactions of this type may equally be used here. Examples of such alkylating agents include: lower alkyl monohalides, such as methyl iodide, methyl bromide, methyl chloride, ethyl iodide, ethyl bromide, ethyl chloride, propyl iodide, propyl bromide, isopropyl bromide, butyl bromide, isobutyl bromide, sec-butyl bromide, t-butyl bromide, pentyl bromide, isopentyl bromide, 2-methylbutyl bromide, neopentyl bromide, 1-ethylpropyl bromide, hexyl bromide, 4-methylpentyl bromide, 3-methylpentyl bromide, 2-methylpentyl bromide, 1-methylpentyl bromide, 3,3-dimethylbutyl bromide, 2,2-dimethylbutyl bromide, 1,1-dimethylbutyl bromide, 1,2-dimethylbutyl bromide, 1,3-dimethylbutyl bromide, 2,3-dimethylbutyl bromide and 2-ethylbutyl bromide; lower alkyl polyhalides, such as trifluoromethyl iodide, trichloromethyl iodide, difluorodibromomethane, chlorodifluoromethane, dichlorodifluoromethane, bromodifluoromethane, bromodichloromethane, bromofluoromethane, bromochloromethane, dibromomethane, 1-bromo-2,2,2-trifluoroethane, 1,2-dibromoethane, 1-bromo-3,3,3-trifluoropropane, 1-bromo-4-fluorobutane and 1-bromo-6,6,6-trifluorohexane; lower dialkyl sulfates, such as dimethyl sulfate and diethyl sulfate; sulfonates, such as methyl trifluoromethanesulfonate, ethyl methanesulfonate, propyl p-toluenesulfonate, isopropyl trifluoromethanesulfonate, sec-butyl methanesulfonate and 1-methylbutyl trifluoromethanesulfonate. Of these, we prefer methyl iodide, methyl bromide and chlorodifluoromethane.

There is likewise no particular restriction on the nature of the cycloalkylating agents used, and any cycloalkylating agent commonly used in reactions of this type may equally be used here. Examples of such cycloalkylating agents include: lower cycloalkyl halides, such as cyclopropyl iodide, cyclopropyl bromide, cyclobutyl iodide, cyclopentyl iodide, cyclopentyl bromide, cyclohexyl iodide, cyclohexyl bromide and cycloheptyl iodide; sulfonates, such as cyclopentyl trifluoromethanesulfonate, cyclohexyl methanesulfonate, cyclohexyl-p-toluenesulfonate and cyclohexyl trifluoromethanesulfonate.

The alkylating agent or cycloalkylating agent is preferably used in an amount of from 1 to 10 equivalents, preferably from 1 to 5 equivalents, per equivalent of the compound of formula (IV).

There is likewise no particular restriction on the nature of the bases used, and any base commonly used in reactions of this type may equally be used here. Examples of such bases include: alkali metal carbonates, such as sodium carbonate or potassium carbonate; alkali metal hydrogencarbonates, such as sodium hydrogencarbonate or potassium hydrogencarbonate; alkali metal hydrides, such as sodium hydride, lithium hydride or potassium hydride; alkali metal hydroxides, such as sodium hydroxide or potassium hydroxide; alkaline earth metal hydroxides, such as barium hydroxide; alkali metal alkoxides, such as sodium methoxide, sodium ethoxide or potassium t-butoxide; organic bases, such as triethylamine, tributylamine, diisopropylethylamine, N-methylmorpholine, pyridine, 4-N,N-dimethylamino) pyridine, N,N-dimethylaniline, N,N-diethylaniline, 1,5-diazabicyclo[4.3.0]non-5-ene, 1,4-diazabicyclo[2.2.2] octane (DABCO) or 1,8-diazabicyclo[5.4.0]undec-7-ene (DBU); and organometallic bases, such as butyllithium or lithium diisopropylamide. Of these, we prefer potassium carbonate and sodium hydride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as hexane, cyclohexane, benzene or toluene; halogenated hydrocarbons, such as methylene chloride, dichloroethane, chloroform or tetrachloroethane; ethers, such as dioxane, diethyl ether, tetrahydrofuran (THF) or ethylene glycol dimethyl ether; amides, such as dimethylformamide (DMF), dimethylacetamide or hexamethylphosphoric triaminide (HMPA); ketones, such as acetone, methyl ethyl ketone, methyl isobutyl ketone or cyclohexanone; nitrites, such as acetonitrile or isobutyronitrile; or esters, such as methyl acetate, ethyl acetate or propyl acetate. Of these, we prefer acetone and DMF.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 150° C., more preferably from −10° C. to 90° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 10 hours, will usually suffice.

Method F

This reaction scheme illustrates the preparation of an indole compound of formula (VII), which is an important intermediate for preparing the compounds of the present invention.

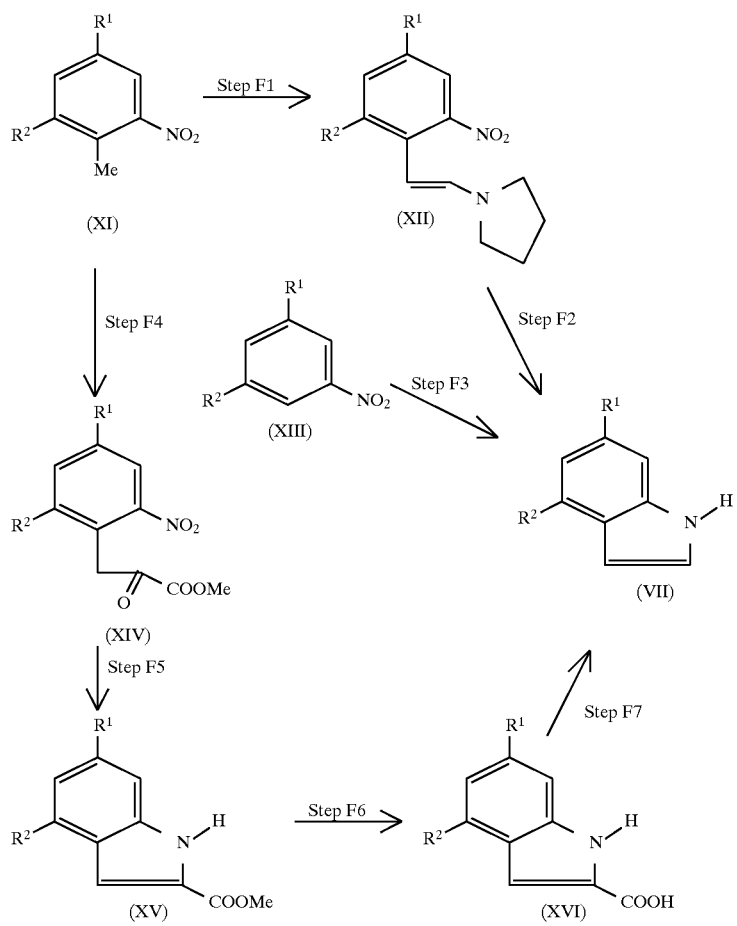

In the above formulae, $R^1$ and $R^2$ are as defined above.

Step F1

In this Step, an enamine compound of formula (XII) is prepared by using an o-methylnitrobenzene compound of formula (XI) as a starting material.

This step can be carried out, for example, by the method described in Paul L. Feldman, Henry Rapoport [Synthesis, 735, (1986)], the disclosures of which are incorporated herein by reference.

Step F2

In this Step, the compound of formula (VII) is prepared by using the compound of formula (XII) as a starting material.

This step is carried out by catalytic reduction in the presence of a palladium-on-carbon catalyst, for example, by the method described in Paul L. Feldman, Henry Rapoport [Synthesis, 735, (1986)] or by reduction with titanium trichloride in the presence of ammonium acetate followed by a dehydration-cyclization reaction using the method described by William A. Ayer et al. [Tetrahedron, Vol.48, No.14, 2919 (1992)], the disclosures of which are incorporated herein by reference.

The compound of formula (VII) can be prepared by reacting the compound of formula (XII) with a Lewis acid (e.g. titanium trichloride) without intermediate isolation after preparation from the compound of formula (XI). This is the same reaction as is described in Step F1.

Step F3

In this Step, the compound of formula (VII) is prepared from a nitrobenzene compound of formula (XIII) by reacting it with an appropriate vinyl Grignard reagent.

This step can be carried out, for example, by the method described by David R. Dobsonn et al. [Synlett., 79(1992)], the disclosures of which are incorporated herein by reference.

Step F4

In this Step, a compound of formula (XIV) is prepared by reacting the o-methylnitrobenzene compound of formula (M) with dimethyl oxalate in the presence of a base.

Step F5

In this Step, a compound of formula (XV) is prepared from the compound of formula (XIV) by cyclizing it with titanium trichloride.

Steps F4 and F5 can be carried out, for example, by the methods (preparation methods of Compound Nos. 72 and 73) described in Japanese Unexamined Patent Publication (Kokai) No. Hei 7-188166.

Step F6

In this Step, a compound of formula (XVI) is prepared using the compound of formula (XV) as a starting material.

This step is a hydrolysis reaction of an ester compound with a base and may be carried out by conventional methods.

The reaction is carried out in the presence of a base. There is no particular restriction on the nature of the bases used, and any base commonly used in reactions of this type may equally be used here. Examples of such bases include: alkali metal carbonates, such as sodium carbonate or potassium carbonate; alkali metal hydrogencarbonates, such as sodium hydrogencarbonate or potassium hydrogencarbonate; alkali metal hydroxides, such as sodium hydroxide or potassium hydroxide; alkaline earth metal hydroxides, such as barium hydroxide; and alkali metal alkoxides, such as sodium methoxide, sodium ethoxide or potassium t-butoxide. Of these, we prefer the alkali metal hydroxides, such as sodium hydroxide or potassium hydroxide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as dioxane, diethyl ether, tetrahydrofuran (TBF) or ethylene glycol dimethyl ether; amides, such as dimethylformamide (DMF), dimethylacetamide or hexamethylphosphoric triamide (HMPA); ketones, such as acetone, methyl ethyl ketone or methyl isobutyl ketone; and nitrites, such as acetonitrile or isobutyronitrile. Of these, we prefer methanol or ethanol.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 30° C. to 150° C., more preferably from 50° C. to 100° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 hour to 5 hours, will usually suffice.

Step F7

In this Step, the compound of formula (VII) is prepared using the compound of formula (XVI) as a starting material.

This step may be carried out, for example, by the method described by Bergmann et al. [J. Chem. Soc., 1913 (1959)], the disclosures of which are incorporated herein by reference.

After completion of any of the above reactions, the desired product of each reaction can be collected from the reaction mixture by conventional means. For example, one suitable recovery technique comprises: neutralising the reaction mixture; removing insolubles, if any, by filtration; and adding a water-immiscible organic solvent, such as ethyl acetate, to the resulting mixture. The resulting mixture is washed with water, the organic layer containing the desired compound is separated and dried over a dehydrating agent, such as anhydrous magnesium sulfate, after which the solvent is removed by distillation under reduced pressure to obtain the desired compound.

The resulting compound can be further purified, if necessary, by conventional means, for example, by recrystallization, reprecipitation, chromatography, or distillation.

Of course, the purification can be stopped at any desired stage of purification and the crude product can be also used as an active ingredient or as a starting compound for a subsequent reaction.

Method G

This provides an alternative, and highly desirable, method of preparing certain compounds of the present invention, specifically those compounds of formula (I) in which $R^1$ represents a fluorine atom, that is a compound of formula (If).

Reaction Scheme G

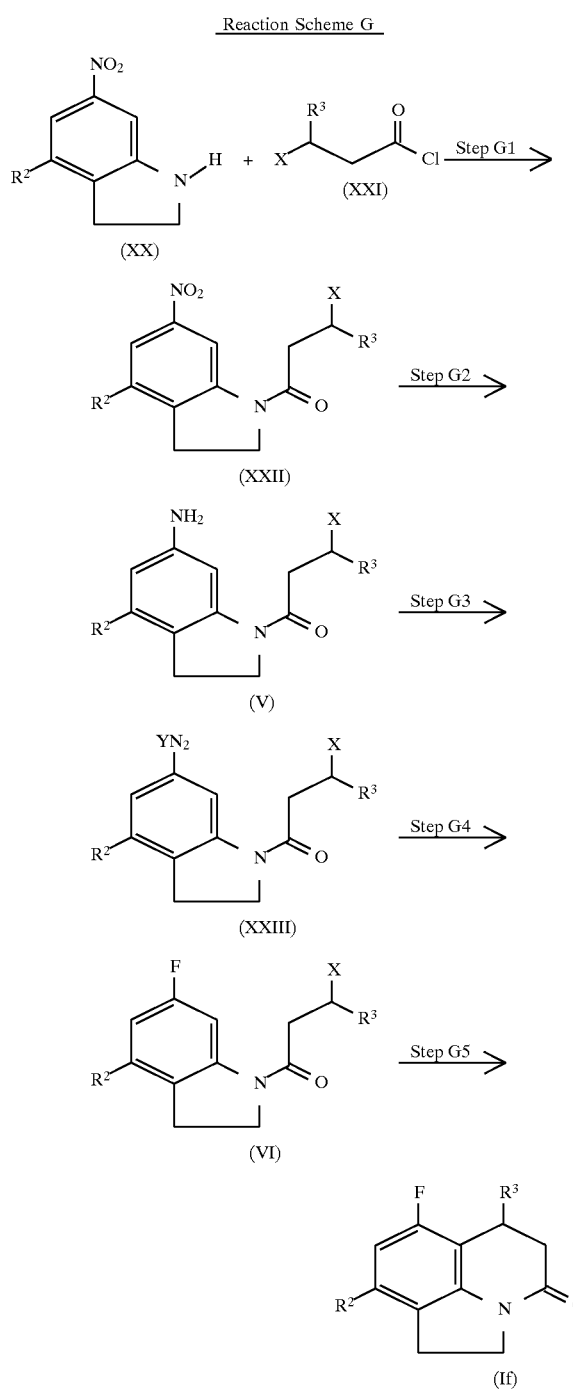

In the above formulae:

$R^2$, $R^3$ and X are as defined above; and

Y represents a fluorine atom, a group of formula $BF_4$, a group of formula $PF_6$, a group of formula $AsF_6$, or a group of formula $SbF_6$.

Step G1

In this Step, a compound of formula (XXII) is prepared by reacting an indoline compound of formula (XX) [which is a known compound; described in the literature, for example Zhur. Obschclei. Khim., 29, 2541 (1959)] with a halogen-substituted propionyl chloride of formula (XXI) in the presence or absence of a base.

The amount of the compound of formula (XXI) used in this step is preferably from 1 to 3 equivalents per equivalent of the compound of formula (XX), more preferably from 1 to 1.5 equivalents.

The presence of a base is not essential in the present step. If used, there is no particular restriction on the nature of the bases used, and any base commonly used in reactions of this type may equally be used here. Examples of such bases include: alkali metal carbonates, such as sodium carbonate or potassium carbonate; an alkali metal hydrogencarbonates, such as sodium hydrogencarbonate or potassium hydrogencarbonate; alkali metal hydrides, such as sodium hydride, lithium hydride or potassium hydride; alkali metal hydroxides, such as sodium hydroxide or potassium hydroxide; alkaline earth metal hydroxides, such as barium hydroxide; alkali metal alkoxides, such as sodium methoxide, sodium ethoxide or potassium t-butoxide; organic bases, such as triethylamine, tributylamine, diisopropylethylamine, N-methylmorpholine, pyridine, 4-(N,N-dimethylamino)-pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU); and organometallic bases, such as butyllithium or lithium diisopropylamide. Of these, we prefer triethylamine.

The amount of the base used in the present step is preferably from 0.01 to 2 equivalents per equivalent of the compound of formula (XX), more preferably from 0.1 to 1 equivalent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as hexane, cyclohexane, benzene or toluene; halogenated hydrocarbons, such as methylene chloride, dichloroethane, chloroform or tetrachloroethane; ethers, such as dioxane, diethyl ether, tetrahydrofuran (THF) or ethylene glycol dimethyl ether; amides, such as dimethylformamide, dimethylacetamide or hexamethylphosphoric triamide (HMPA); ketones, such as acetone, methyl ethyl ketone, methyl isobutyl ketone or cyclohexanone; nitriles, such as acetonitrile or isobutyronitrile; and esters, such as methyl acetate, ethyl acetate or propyl acetate. Of these, we prefer acetone.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 150° C., more preferably from 10° C. to 90° C. The time required for the reaction may also vary widely, depending on many factors, notably the reaction temperature, the presence or absence, and amount, of the base and the nature of the reagents and solvent employed. However, provided that the reaction is effected under the preferred conditions outlined above, a period of from 10 minutes to 24 hours, more preferably from 30 minutes to 10 hours, will usually suffice.

Step G2

In this Step, a compound of formula (V) is prepared by reducing the nitro group of a compound of formula (XXII) to an amino group.

The reduction can be carried out catalytically using a catalyst and hydrogen gas as is used in conventional reduction in the presence of an appropriate solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol, 2-propanol or propanol; esters, such as ethyl acetate or butyl acetate; ethers, such as tetrahydrofuran or diethyl ether; organic acids, such as formic acid or acetic acid; or a mixture of any two or more of these solvents. Of these, we prefer ethanol or acetic acid.

There is no particular restriction on the nature of the catalysts used, and any catalyst commonly used in conventional catalytic reduction reactions of this type may equally be used here. Examples of such catalysts include: 5% to 10% by weight palladium-on-carbon (Pd-C), platinum-on-carbon (Pt-C) and platinum oxide ($PtO_2$).

The amount of the catalyst used is preferably from 1/200 mol % to 1/50 mol %, more preferably about 1/100 mol %.

The reaction proceeds under superatmospheric or atmospheric conditions, preferably at from 3 to 15 atmospheres, more preferably at 4 to 5 atmospheres.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 30° C. to 60° C. The time required for the reaction may also vary widely, depending on many factors, notably the reaction temperature and the nature of the reagents and solvent employed. However, provided that the reaction is effected under the preferred conditions outlined above, a period of from 30 minutes to 10 hours will usually suffice.

Alternatively, the reduction of the present step, can be carried out using an acid and a metal or a halogenated metal. In this case, suitable acids include inorganic acids, such as concentrated sulfuric acid, concentrated nitric acid and concentrated hydrochloric acid, and organic acids, such as acetic acid, preferably concentrated hydrochloric acid or acetic acid. The metal or halogenated metal which may be employed includes zinc (Zn), lead (Pb), iron (Fe), tin (II) chloride ($SnCl_2$), etc., preferably zinc, iron or $SnCl_2$. The combination of the acid and the metal or the halogenated metal preferably includes a combination of concentrated hydrochloric acid and $SnCl_2$, that of acetic acid and zinc and that of acetic acid and iron.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol, 2-propanol or propanol; esters, such as ethyl acetate or butyl acetate; ethers, such as tetrahydrofuran or diethyl ether; organic acids, such as formic acid or acetic acid; or a mixture of any two or more of these solvents, more preferably methanol or acetic acid.

The amount of the metal used is preferably from 1 to 10 equivalents per equivalent of the compound of formula (XXII), more preferably from 1 to 5 equivalents.

The amount of the acid used is preferably from 3 to 500 equivalents per equivalent of the compound of formula (XXI), more preferably from 5 to 150 equivalents.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 30° C. to 150° C., more preferably from 40° C. to 100° C. The time required for the reaction may also vary widely, depending on many factors, notably the reaction temperature and the nature of the reagents and solvent employed. However, provided that the reaction is effected under the preferred conditions outlined above, a period of from 10 minutes to 10 hours, more preferably from 30 minutes to 3 hours, will usually suffice.

Step G3

In this Step, a compound of formula (V) is converted into a diazonium salt of formula (XXIII).

This step may be accomplished by adding a diazotizing agent and a source of fluorine in the presence of an appropriate solvent and in the presence or absence of an acid.

There is no particular restriction on the nature of the diazotizing agents used, provided that it can diazotize an amino group, and any diazotizing agent commonly used in reactions of this type may equally be used here. Examples of such diazotizing agents include: nitrites, such as sodium nitrite, potassium nitrite or silver nitrite; alkyl nitrites, such as ethyl nitrite or isoamyl nitrite; and nitrous acid; preferably sodium nitrite or isoamyl nitrite.

The amount of the diazotizing agent used is usually from 1 to 3 equivalents per equivalent of the compound of formula (V), preferably from 1 to 1.5 equivalents.

The source of fluorine employed here is not particularly critical, so long as it releases a fluoride anion, and examples include: hydrofluoric acids, such as fluoboric acid ($HBF_4$), hexafluorophosphoric acid ($HPF_6$), $HASF_6$, fluoroantimonic acid ($HSbF_6$) or hydrofluoric acid; or tetrafluoroborates, such as sodium tetrafluoroborate ($NaBF_4$), ammonium tetrafluoroborate ($NH_4BF_4$) or potassium tetrafluoroborate ($KBF_4$). Of these, we prefer $HBF_4$ or HF.

The amount of the source of fluorine used is usually from 1 to 200 equivalents per equivalent of the compound of formula (V), more preferably from 1 to 150 equivalents.

Alternatively, nitrosonium tetrafluoroborate ($NOBF_4$), in which the diazotizing agent and the source of fluorine are combined, can be used.

The amount of $NOBF_4$ used is usually from 1 to 3 equivalents per equivalent of the compound of formula (V), more preferably from 1 to 1.5 equivalents.

In general, we prefer that the diazotizing agent should be added to the reaction mixture first, followed by the source of fluorine. However, if desired, the source of fluorine may be added first, followed by the diazotizing agent, or the diazotizing agent and the source of fluorine may be added simultaneously.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated aromatic hydrocarbons, such as chlorobenzene or dichlorobenzene; aromatic hydrocarbons, such as benzene or toluene; hydrocarbons, such as hexane, pentane or octane; aromatic heterocyclic compounds, such as pyridine, 2-hydroxypyridine or pyrazine; ethers, such as tetrahydrofuran or diethyl ether; amides, such as dimethylformamide (DMF) or N,N-dimethylacetamide; or water. Where the diazotizing agent used is a nitrite or nitrous acid, pyridine or water are preferably used as the solvent. Where the diazotizing agent used is an alkyl nitrite, DMF is preferably used or where the diazotizing agent used is $NOBF_4$, dichlorobenzene is preferably used.

There is no particular restriction on the nature of the acids used so long as it can convert the compound of formula (V)

to a salt, and any acid commonly used in reactions of this type may equally be used here. Examples of such acids include: hydrochloric acid, fluoboric acid, hydrofluoric acid, nitrous acid, and nitrosylsulfuric acid. Of these, we prefer hydrochloric acid, fluoboric acid or hydrofluoric acid.

In some cases, the source of fluorine may function simultaneously as an acid. Examples of such compounds include fluoboric acid, and hydrofluoric acid.

The amount of the acid used is preferably from 3 to 500 equivalents per equivalent of the compound of formula (V), more preferably from 5 to 150 equivalents.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 50° C., more preferably from 0° C. to 20° C. The time required for the reaction may also vary widely, depending on many factors, notably the reaction temperature, the presence or absence and amount of the acid and the nature of the reagents and solvent employed. However, provided that the reaction is effected under the preferred conditions outlined above, a period of from 10 minutes to 5 hours, more preferably from 30 minutes to 3 hours, will usually suffice.

After completion of the reaction, the compound of formula (XXII) can be isolated by collecting the crystallised solid by filtration or by concentrating the solvent. However, it can be used for a subsequent reaction without isolation.

Step G4

In this Step, a compound of formula (VI) is prepared by heating the compound of formula (XXIII).

This step can be carried out in the presence or absence of an appropriate solvent. Where a solvent is used, this can be the solvent used in Step G3 or a solvent which is newly added in the present step.

There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene, xylene or biphenyl; halogenated aromatic hydrocarbons, such as dichlorobenzene or chlorobenzene; aromatic heterocyclic compounds, such as quinoline, pyridine or pyrazine; halogenated hydrocarbons, such as methylene chloride, chloroform, carbon tetrachloride, dichloroethane, chlorobenzene or dichlorobenzene; ethers, such as diethyl ether, diisopropyl ether, tetrahydrofuran, dioxane, dimethoxyethane, diethylene glycol dimethyl ether or petroleum ether; nitriles, such as acetonitrile or isobutyronitrile; amides, such as dimethylformamide (DMF) or N,N-dimethylacetamide; and hydrocarbons, such as hexane, heptane, octane or dodecane. Of these, we prefer dichlorobenzene, toluene, biphenyl, pyridine, petroleum ether, heptane or dodecane, more preferably dichlorobenzene, heptane or pyridine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 40° C. to 200° C., more preferably from 60° C. to 100° C. The time required for the reaction may also vary widely, depending on many factors, notably the reaction temperature and the nature of the reagents and solvent employed. However, provided that the reaction is effected under the preferred conditions outlined above, a period of from 1 hour to 10 hours, more preferably from 1 hour to 4 hours, will usually suffice.

Step G5

In this Step, a compound of formula (If) is prepared by carrying out a ring closure of the compound of formula (VI).

This step may be carried out under the same conditions as described above in relation to Step A4.

After completion of each reaction mentioned above, the desired compound of each reaction can be collected from the reaction mixture by conventional means.

For example, one suitable recovery procedure comprises: appropriately neutralising the reaction mixture; removing the insolubles, if any, by filtration; adding a water-immiscible organic solvent such as ethyl acetate; washing the organic layer with water; separating the organic layer containing the desired compound; drying it over anhydrous magnesium sulfate; and distilling off the solvent.

The resulting compound can be further purified, if necessary, by ordinary methods, for example, recrystallization, reprecipitation or chromatography.

Of course, the purification can be stopped at any stage of the purification and the crude product can be used as an active ingredient or a starting compound for the subsequent reaction.

The compounds of the present invention may be used as such or in admixture with one or more other materials, which can be active compounds or carriers or the like to form a composition. Such compositions may be any form well known for use for fungicides used in agriculture, for example, dusts, crude dusts, fine granules, granules, wettable powders, suspension concentrates, emulsion concentrates, water-soluble liquids, water-soluble agents, oil suspension agents and capsule agents with a polymer substance and may include a carrier and, if necessary other auxiliary agents.

The carrier may be a synthetic or natural inorganic or organic substance which is mixed in a fungicide for agriculture in order to make the active ingredient more accessible, to make it easier to divide the active compound into portions to be treated or to make storage, transportation or handling of the active ingredients easy.

Suitable solid carriers include, for example: inorganic substances, such as clays (for example kaolinite, pyrophylite, montmorillonite or attapulgite), talc, mica, pyrophylite, Sirasu, pearlite, pumice, vermiculite, gypsum, calcium carbonate, dolomite, diatomaceous earth, magnesium lime, phosphor lime, zeolite, silicic anhydride and synthetic calcium silicate; vegetable organic substances, such as soybean powder, tobacco powder, walnut powder, wheat powder, wood flour, cork, starch and crystal cellulose; synthetic or natural high molecular compounds, such as cumarone resins, petroleum resins, alkyd resins, polyvinyl chloride, polyalkylene glycol, ketone resins, ester gums, copal gums and dammar gums; waxes, such as carnauba wax and bees wax; or urea.

Suitable liquid carriers include, for example: paraffin type or naphthene type hydrocarbons, such as kerosine, mineral oil, spindle oil and white oil; aromatic hydrocarbons, such as benzene, toluene, xylene, ethylbenzene, cumene and methylnaphthalene; chlorinated hydrocarbons, such as carbon tetrachloride, chloroform, trichloroethylene, monochlorobenzene and o-chlorotoluene; ethers, such as dioxane and tetrahydrofuran; ketones, such as acetone, methyl ethyl ketone, diisobutyl ketone, cyclohexanone, acetophenone and isophorone; esters, such as ethyl acetate, amyl acetate, ethylene glycol acetate, diethylene glycol acetate, dibutyl maleate and diethyl succinate; alcohols, such as methanol, hexanol, ethylene glycol, diethylene glycol, cyclohexanol and benzyl alcohol; ether alcohols, such as ethylene glycol ethyl ether, ethylene glycol phenyl ether, diethylene glycol ethyl ether and diethylene glycol butyl ether; polar solvents, such as dimethylformamide and dimethyl sulfoxide; and water.

The composition may, if desired, also include a surface active agent for the purpose of emulsification, dispersion, wetting, extension, bonding, disintegration control, stabilisation of the active ingredient, improvement of fluidity or corrosion prevention. This may be a non-ionic, anionic, cationic or amphoteric ionic substance. However, a non-ionic and/or anionic substance are/is usually used.

Suitable non-ionic surface active agents include, for example: a substance obtained by carrying out addition polymerisation of a higher aliphatic alcohol, such as lauryl alcohol, stearyl alcohol or oleyl alcohol, with ethylene oxide; a substance obtained by carrying out addition polymerisation of an alkylphenol, such as isooctylphenol or nonylphenol, with ethylene oxide; a substance obtained by carrying out addition polymerisation of an alkylnaphthol, such as butylnaphthol or octylnaphthol, with ethylene oxide; a substance obtained by carrying out addition polymerisation of a higher fatty acid, such as palmitic acid, stearic acid or oleic acid, with ethylene oxide; a substance obtained by carrying out addition polymerisation of a mono- or dialkylphosphoric acid, such as stearylphosphoric acid or dilaurylphosphoric acid, with ethylene oxide; a substance obtained by carrying out addition polymerisation of an amine, such as dodecylamine or stearic acid amide, with ethylene oxide; a higher fatty acid ester of a polyhydric alcohol, such as sorbitan; and a substance obtained by carrying out addition polymerisation thereof with ethylene oxide; a substance obtained by carrying out addition polymerisation of ethylene oxide and propylene oxide, acetylene alcohol, acetylene diol; and an acetylene type surface active agent obtained by carrying out addition polymerisation thereof with alkylene oxide; a silicone type surface active agent containing polyether modified silicone oil as a main component, etc.

Suitable anionic surface active agents include, for example: alkylsulfuric acid ester salts, such as sodium laurylsulfate or oleyl alcohol sulfuric acid ester amine salt; alkyl sulfonates, such as sodium sulfosuccinic acid dioctyl ester or sodium 2-ethylhexenesulfonate; and aryl sulfonates, such as sodium isopropylnaphthalenesulfonate, sodium methylenebisnaphthalenesulfonate, sodium ligninsulfonate or sodium dodecylbenzenesulfonate. A fluorine type surface active agent can be also used in which a part of the hydrogen atoms of these various surface active agents is replaced by a fluorine atom.

Moreover, the fungicidal compositions of the present invention may optionally contain a high-molecular weight compound, such as casein, gelatin, albumin, hide glue, sodium alginate, carboxymethyl cellulose, methyl cellulose, hydroxyethyl cellulose or polyvinyl alcohol, and, if desired, other auxiliary agents in order to improve the properties of the preparations and enhance the biological effect thereof.

A single one of the above-mentioned carriers and various other auxiliary agents may be used or a combination of any two or more of these may be used, depending on the purpose taking into consideration the forms of the preparations and the methods employed to apply the preparations.

Dusts usually contain from 0.1 to 25 parts by weight of the active ingredient, the remaining portion being a solid carrier.

Wettable powders usually contain from 1 to 80 parts by weight of the active ingredient, the remaining portion being a solid carrier and a dispersion-wetting agent, and, if necessary, a protective colloid, a thixotropic agent, an anti-foaming agent and the like may be added.

Granules usually contain, for example, from 1 to 35 parts by weight of the active ingredient, most of the remaining portion being a solid carrier.

When the compound of the present invention is used, it can be mixed with other fungicides, insecticides, acaricides, nematocides, herbicides, plant growth regulators, fertilisers, soil improving agents and the like to improve its effectiveness range and achieve labor-saving.

The amount to be applied varies depending on the weather conditions, the form of the formulation, application timing, the application method, the place, the target disease injury, the target crop and the like. However, we generally prefer to use from 0.1 g to 100 g per one are, more preferably from 5 g to 40 g of the active ingredient. Emulsions, wettable powders and suspensions are generally applied by diluting a predetermined amount of the active compound with from 1 liter to 10 liters of water per one are (if necessary, a surface active agent, polyoxyethylene resin acid, ligninsulfonic acid salt, abietic acid salt, dinaphthylmethanedisulfonic acid salt or a spreader such as paraffin can be added). Granules and the like are usually applied without diluting.

The compound of the present invention may be employed in admixture with appropriate water repellents, foaming agents, extenders, etc. in the form of agricultural chemical formulations (granules, tablets, wettable powders, capsules, etc.) which are easily dispersed or dissolved in water or on the surface of water for the purpose of labor-saving, safety and the like, and the mixture is packaged with a water-soluble film (or bag) and it is also possible to directly throw it into water. Moreover, it is possible to apply the present compound in a seeding box of rice.

The above-mentioned formulations are applied as such or after diluting them with water and the like to plants or the surface of water or the soil. That is, the above-mentioned formulations can be used in various forms by spraying or powder-spraying them to plants, spraying, powder-spraying or granule-spraying them to the surface of water or the surface of the soil in a paddy field or, if necessary, mixing them with the soil after the application.

The biological activity of the compounds of the present invention is illustrated by the following Experiment.

EXPERIMENT

Rice blast (*Pyricularia oryzae*) control test (protective effect)

Rice seedlings at the 3–4 leaf stage growing in a plastic pot of 25 cm$^2$ were maintained under irrigation conditions at a water depth of 2 cm and a predetermined amount (50 g a.i./10a) of the compound to be tested which was formulated in the form of wettable powder as described hereafter in Formulation 2 was suspended in water and applied to the pot. The rice seedling was then placed in a glass greenhouse for 7 days, after which it was inoculated with a conidiospore suspension of *Pyricularia oryzae* by spraying. After inoculation, the rice seedling was placed in a chamber maintained at a temperature of 20° to 22° C. and a relative humidity of 100% for 6 days and thereafter the number of lesions formed on the upper 2 leaves was examined and a control value was obtained according to the following equation.

$$\text{Control value } (\%) = \{(N_o - N_a)/N_o\} \times 100$$

where $N_o$ is the number of lesions at the section to which the test compound was not applied; and
$N_a$ is the number of lesions at the section to which the test compound was applied.

The results are shown in Table 6.

The Comparative compounds referred to in the Table are listed below:

Comparative compound 1

This compound is commercially available under the common name "Pyroquilone". The effect of the compound against rice blast is described in Japanese Patent Publication (Kokoku) No. Sho 52-48176. This compound is also described as No. 20 in J. Agric. Food Chem., Vol. 29, No. 3, 576–579 (1981).
1,2,5,6-Tetrahydro-4H-pyrrolo[3,2,1-ij]quinolin-4-one Comparative compound 2
8-Fluoro-1,2,5,6-tetrahydro-4H-pyrrolo[3,2,1-ij]quinolin-4-one Comparative compound 3
8-Chloro-1,2,5,6-tetrahydro-4H-pyrrolo[3,2,1-ij]quinolin-4-one Comparative compound 4
8-Methyl-1,2,5,6-tetrahydro-4H-pyrrolo[3,2,1-ij]quinolin-4-one Comparative compound 5
8-Methoxy-1,2,5,6-tetrahydro-4H-pyrrolo[3,2,1-ij]quinolin-4-one Comparative compound 6
8-Difluoromethoxy-1,2,5,6-tetrahydro-4H-pyrrolo[3,2,1-ij]quinolin-4-one Comparative compound 7
The effect of this compound against rice blast is described in Japanese Patent Publication (Kokoku) No. Sho 52-48176.
6-Methyl-1,2-dihydro-4H-pyrrolo[3,2,1-ij]quinolin-4-one Comparative compound 8
This compound is described in Japanese Unexamined Patent Publication (Kokai) No. Sho 54-163813.
6-Methyl-1,2,5,6-tetrahydro-4H-pyrrolo[3,2,1-ij]quinolin-4-one.

The compounds of the present invention are identified by the number of the Example appearing hereafter in which their preparation is described and by the number assigned to them in the foregoing Tables 1 and 2.

TABLE 6

| Example No. (Compound No.) | Control value |
| --- | --- |
| Example 1 (1) | 100 |
| Example 2 (2) | 90 |
| Example 3 (39) | 90 |
| Example 4 (5) | 80 |
| Example 5 (17) | 70 |
| Example 6 (37) | 80 |
| Example 7 (269) | 70 |
| Example 8 (289) | 90 |
| Example 10 (253) | 90 |
| Comparative compound 1 | 30 |
| Comparative compound 2 | 30 |
| Comparative compound 3 | 30 |
| Comparative compound 4 | 0 |
| Comparative compound 5 | 0 |
| Comparative compound 6 | 30 |
| Comparative compound 7 | 0 |
| Comparative compound 8 | 10 |

The structural formulae of the compounds in Table 6 are shown below.

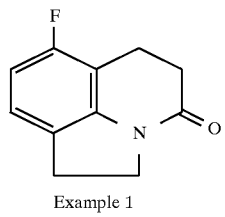

Example 1

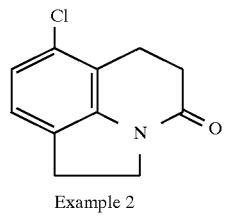

Example 2

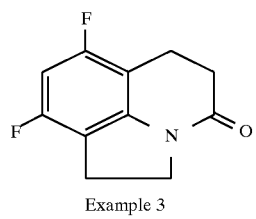

Example 3

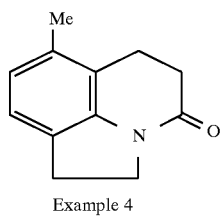

Example 4

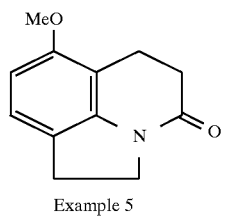

Example 5

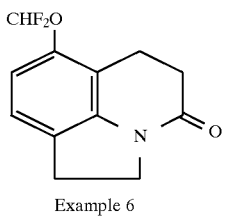

Example 6

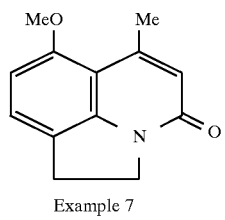

Example 7

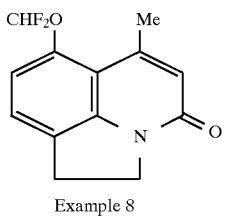

Example 8

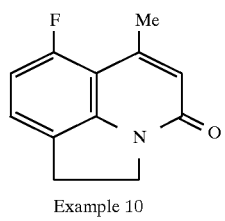

Example 10

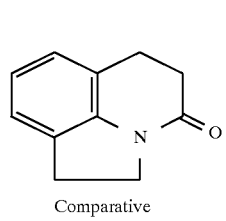

Comparative Compound 1

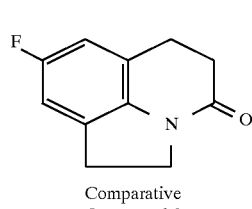

Comparative Compound 2

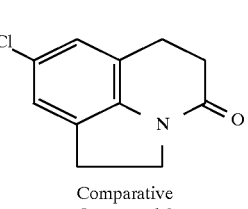

Comparative Compound 3

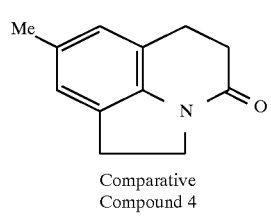

Comparative Compound 4

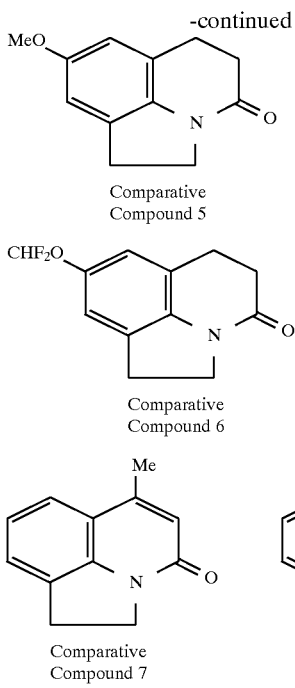

Comparative Compound 5

Comparative Compound 6

Comparative Compound 7

Comparative Compound 8

As can be seen from the above results, the compounds of the present invention have excellent fungicidal activity, very substantially better than that even of structurally very similar compounds. Accordingly, these compounds are useful as agricultural and horticultural fungicides against various plant pathogenic fungi, particularly rice blast (*Pyricularia oryzae*). Moreover, the compounds of the present invention have no adverse effects on the plants, and so can be used freely, without the risk of damaging the plants to be treated. The compounds of the present invention are effective systemically and can thus be used to treat plants to control many diseases caused by plant pathogens, including rice blast (*Pyricularia oryzae*) not only by foliar application but also by application to the water surface of, for example, paddy fields.

Plant diseases against which the compounds of the present invention exhibit an excellent effect may include, for example, rice blast (*Pyricularia oryzae*), leaf spots (*Cochliobolus miyobeanus, Helminthosporium, sigmoideum* var. *irregulare, Sphaerulina oryzine*), Cucumber anthracnose (*Colletotrichum lagenarium*) and the like, but the fungicidal spectrum of the compound of the invention is not limited merely to these diseases.

The preparation of compounds of the present invention is further illustrated by the following non-limiting Examples. The preparation of certain of the starting materials used in these Examples is illustrated by the subsequent Preparations.

EXAMPLE 1

7-Fluoro-1,2,5,6-tetrahydro-4H-pyrrolo[3,2,1-ij]quinolin-4-one (Compound No. 1)

1(1) 3-Fluoro-6(methoxalylmethyl)-1-nitrobenzene 45.8 g (0.400 mol) of t-butoxypotassium were added to 100 ml of methanol, while ice-cooling, and then 52.9 g (0.448 mol) of dimethyl succinate were added to the resulting mixture, while stirring. A solution of 6.20 g (40.0 mmol) of 4-fluoro-2-nitrotoluene in 20 ml of methanol was then added dropwise at room temperature to the mixture, and the mixture was stirred at the same temperature for 4 hours. At the end of this time, sufficient of a 10% w/v aqueous solution of potassium hydrogensulfate was added to the reaction mixture to make it acidic, and thereafter the resulting mixture was extracted with ethyl acetate. The organic extract was then washed with water and with a small amount of a 1% w/v aqueous solution of sodium carbonate, in that order, after which it was dried over anhydrous magnesium sulfate. The mixture was filtered, and then the solvent was removed by distillation under reduced pressure, to obtain 9.85 g (crude yield: 102%) of the crude title compound as an oily substance. The crude title compound was a mixture (about 1:1) of the keto form and the enol form of the title compound.

Mass spectrum (MS) m/z: 241 (M+), 211, 182, 154, 137, 123, 108, 107. $^1$H-Nuclear Magnetic Resonance Spectrum (200 MHz, CDCl$_3$) δ ppm: 8.28 (doublet of doublets, J=5.6 & 8.9 Hz); 7.92 (doublet of doublets, J=2.2 & 8.4 Hz); 7.66 (doublet of doublets, J=2.6 & 8.4 Hz); 7.38–7.29 (multiplet); 6.90 (singlet); 6.68 (broad singlet); 4.53 (singlet); 3.95 (singlet); 3.94 (singlet).

1(2) 6-Fluoro-2-methoxycarbonylindole

A 24% w/v aqueous solution containing 180 g of titanium chloride was added dropwise to a solution of 9.85 g of crude 3-fluoro-6-(methoxalylmethyl)-1-nitrobenzene [prepared as described in step (1) above] in 190 ml of acetone at room temperature, and the mixture was stirred at room temperature overnight. At the end of this time, the reaction mixture was poured into ice, and the mixture was extracted with ethyl acetate. The extract was then washed with water and dried over anhydrous magnesium sulfate, after which it was filtered, and the solvent was removed by distillation under reduced pressure, to obtain 6.99 g (crude yield: 90.5%) of the crude title compound as crude crystals. These crude crystals were washed with diisopropyl ether and with a small amount of ethyl acetate to obtain 3.16 g (yield: 40.9%) of the title compound as an orange-colored powder.

Mass Spectrum m/z: 193 (M$^+$), 161, 133. $^1$H Nuclear Magnetic Resonance (200 MHz, CDCl$_3$) δ ppm: 8.94 (1H, broad singlet); 7.63 (1H, doublet of doublets, J=5.5 & 9.0 Hz); 7.20 (1H, doublet, J=2.3 Hz); 7.09 (1H, doublet of doublets, J=2.3 & 9.0 Hz); 6.94 (1H, doublet of triplets, J=2.3 & 9.0 Hz); 3.95 (3H, singlet).

1(3) 2-Carboxy-6-fluoroindole 1.54 ml of a 2N aqueous solution of sodium hydroxide (containing 3.08 mmol of sodium hydroxide) were added to a solution of 497.2 mg (2.57 mmol) of 6-fluoro-2-methoxycarbonylindole [prepared as described in step (2) above] in 11 ml of ethanol, and the mixture was stirred at 70° C. for 2 hours. At the end of this time, the reaction mixture was poured into ice-water and acidified with hydrochloric acid. The resulting precipitated solids were collected by filtration and dissolved in ethyl acetate, after which the resulting solution was dried over anhydrous magnesium sulfate. Solids were removed by filtration, and the solvent was removed by distillation under reduced pressure, to obtain 413.9 mg (yield: 89.8%) of the title compound as a white powder.

Mass Spectrum m/z: 179 (M$^+$), 167, 161, 149, 133. $^1$H Nuclear Magnetic Resonance (200 MHz, CD$_3$OD) δ ppm: 7.63 (1H, doublet of doublets, J=5.6 & 9.3 Hz); 7.15 (1H, singlet); 7.12 (1H, doublet of doublets, J=2.2 & 10.3 Hz); 6.88 (1H, doublet of triplets, J=2.2 & 9.3 Hz).

1(4) 6-Fluoroindole 404.6 mg (2.26 mmol) of 2-carboxy-6-fluoroindole [prepared as described in step (3) above] were placed in a pear-shaped flask, and the flask was heated in an oil bath at 260° C. for 3 hours. At the end of this time, the reaction product was purified by preparative thin layer chromatography on silica gel, using a 4:1 by volume mixture of hexane and ethyl acetate as developing solvent, [silica gel plate, thickness: 0.5 mm, 20 cm×20 cm, 4 sheets], to obtain 81.2 mg (yield: 26.6%) of the title compound as an amorphous substance.

$^1$H Nuclear Magnetic Resonance (200 MHz, CDCl$_3$) δ ppm: 8.18 (1H, broad singlet); 7.56 (1H, doublet of doublets, J=5.3 & 8.9 Hz); 7.20–7.17 (1H, multiplet); 7.08 (1H, doublet of doublets, J=2.3 & 9.7 Hz); 6.91 (1H, doublet of triplets, J=2.3 & 8.9 Hz); 6.56–6.53 (1H, multiplet).

1(5) 6-Fluoroindoline 76.9 mg (0.57 mmol) of 6-fluoroindole [prepared as described in step (4) above] were dissolved in 1.5 ml of acetic acid, and 107.5 mg (1.76 mmol) of sodium cyanoborohydride were added to the resulting solution, while ice-cooling and stirring. The mixture was stirred for 30 minutes while cooling so that the internal temperature of the mixture did not exceed 20° C. At the end of this time, the reaction mixture was diluted with 7.5 ml of water and then made alkaline by adding pellets of sodium hydroxide. It was then extracted with ethyl acetate. The organic extract was washed with water and with a saturated aqueous solution of sodium chloride, after which it was dried over anhydrous potassium carbonate. The mixture was filtered, after which the solvent was removed by distillation under reduced pressure, to obtain 65.7 mg (yield: 84.2%) of the title compound as a yellow oily substance.

Mass Spectrum m/z: 137 (M$^+$), 136. $^1$H Nuclear Magnetic Resonance (200 MHz, CDCl$_3$) δ ppm: 7.00 (1H, triplet, J=8.2 Hz); 6.41–6.29 (2H, multiplet); 3.83 (1H, broad singlet); 3.60 (2H, triplet, J=8.4 Hz); 2.98 (2H, triplet, J=8.4 Hz).

1(6) 1-(3-Chloropropionyl)-6-fluoroindoline 64 mg (0.67 mmol) of 3-chloropropionyl chloride were added at room temperature to a solution of 88.2 mg (0.64 mmol) of 6-fluoroindoline [prepared as described in step (5) above] in 17 ml of acetone, and the mixture was heated under reflux for 2 hours. At the end of this time, the reaction mixture was poured into 10% w/v aqueous hydrochloric acid, and the solids which precipitated were collected by filtration. The residue was then extracted with ethyl acetate. The resulting organic extract was washed with water and then dried over anhydrous magnesium sulfate. The mixture was filtered, and then the solvent was removed by distillation under reduced pressure, to obtain 128.6 mg (yield: 87.8%) of the title compound as a pale yellow powder.

Mass Spectrum m/z: 227 (M$^+$), 137, 136. $^1$H Nuclear Magnetic Resonance (200 MHz, CDCl$_3$) δ ppm: 7.98 (1H, doublet of doublets, J=2.4 & 10.6 Hz); 7.09 (1H, doublet of doublets, J=5.5 & 8.3 Hz); 6.72 (1H, doublet of triplets, J=2.4 & 8.3 Hz); 4.12 (2H, triplet, J=8.5 Hz); 3.90 (2H, triplet, J=6.8 Hz); 3.18 (2H, triplet, J=8.5 Hz); 2.91 (2H, triplet, J=6.8 Hz).

1(7) 7-Fluoro-1,2,5,6tetrahydro-4H-pyrrolo[3,2,1-ij] quinolin-4-one (Compound No. 1)

123.2 mg (0.54 mmol) of 1-(3-chloropropionyl)-6-fluoroindoline [prepared as described in step (6) above] were mixed with 361.1 mg (2.71 mmol) of anhydrous aluminum chloride powder, and the mixture was heated at 120° C. for 4 hours. At the end of this time, the reaction mixture was poured into an ice-acid mixture consisting of 10 g of ice and 0.5 ml of 10% aqueous hydrochloric acid, and the mixture was extracted with ethyl acetate, after which it was dried over anhydrous magnesium sulfate. The mixture was filtered, and then the solvent was removed by distillation under reduced pressure. The crude title compound thus obtained was then purified by preparative thin layer chromatography over silica gel, using a 1:1 by volume mixture of hexane and ethyl acetate as developing solvent, [plate, thickness: 0.5 mm, 20 cm×20 cm, 4 sheets], to obtain 52.8 mg (yield: 51%) of the title compound as a powder, melting at 91°–110C.

Mass Spectrum m/z: 191 (M$^+$), 162, 148, 135. $^1$H Nuclear Magnetic Resonance (200 MHz, CDCl$_3$) δ ppm: 6.99 (1H, doublet of doublets, J=4.8 & 8.2 Hz); 6.63 (1H, doublet of doublets, J=9.6 & 8.2 Hz); 4.11 (2H, triplet, J=8.5 Hz); 3.14 (2H, triplet, J=8.5 Hz); 2.99 (2H, triplet, J=7.8 Hz); 2.68 (2H, triplet, J=7.8 Hz).

EXAMPLE 2

7-Chloro-1,2,5,6-tetrahydro-4H-pyrrolo[3,2,1-ij] quinolin-4-one (Compound No. 2)

2(1) 3-Chloro-6-(methoxalylmethyl)-1-nitrobenzene

The procedure described in Example 1(1) was repeated, but using 6.86 g (40.0 mmol) of 4-chloro-2-nitrotoluene as the starting material, to obtain 9.63 g (yield: 93.5%) of the title compound as a pale brown powder. The title compound was the enol form.

Mass Spectrum m/z: 257 (M$^+$), 198, 170, 153. $^1$H Nuclear Magnetic Resonance (200 MHz, CDCl$_3$) δ ppm: 8.22 (1H, doublet, J=8.7 Hz); 7.94 (1H, doublet, J=2.2 Hz); 7.58 (1H, doublet of doublets, J=2.2 & 8.7 Hz); 6.89 (1H, singlet); 6.72 (1H, singlet); 3.98 (3H, singlet).

2(2) 6-Chloro-2-methoxycarbonylindole

The procedure described in Example 1(2) was repeated, but using 1.51 g (6.20 mmol) of 3-chloro-6-(methoxalylmethyl)-1-nitrobenzene [prepared as described in step (1) above] as the starting material, to obtain 0.40 g (yield: 30.8%) of the title compound as a white powder.

Mass Spectrum m/z: 209 (M$^+$), 177, 149, 114. $^1$H Nuclear Magnetic Resonance (200 MHz, CDCl$_3$) δ ppm: 8.91 (1H, broad singlet); 7.61 (1H, doublet, J=8.6 Hz); 7.43 (1H, singlet); 7.19 (1H, doublet, J=2.0 Hz); 7.14 (1H, doublet, J=8.6 Hz); 3.96 (3H, singlet).

2(3) 2-Carboxy-6-chloroindole

The procedure described in Example 1(3) was repeated, but using 407.8 mg (1.95 mmol) of 6-chloro-2-methoxycarbonylindole [prepared as described in step (2) above] as the starting material, to obtain 382.0 mg (a quantitative yield) of the title compound as a white powder.

Mass Spectrum m/z: 195 (M$^+$), 177, 149, 114. $^1$H Nuclear Magnetic Resonance (200 MHz, CD$_3$OD) δ ppm: 11.36 (1H, broad singlet); 7.61 (1H, doublet, J=8.6 Hz); 7.45 (1H, singlet); 7.15 (1H, singlet); 7.06 (1H, doublet, J=8.6 Hz).

2(4) 6-Chloroindole

The procedure described in Example 1(4) was repeated, but using 382.0 mg (2.52 mmol) of 2-carboxy-6-chloroindole [prepared as described in step (3) above] as the starting material, to obtain 62.7 mg (yield: 16.4%) of the title compound as a brown amorphous substance.

$^1$H Nuclear Magnetic Resonance (200 MHz, CDCl$_3$) δ ppm: 8.14 (1H, broad singlet); 7.55 (1H, doublet of doublets, J=1.9 & 8.5 Hz); 7.39 (1H, singlet); 7.22–7.18 (1H, multiplet); 7.10 (1H, doublet of doublets, J=1.9 & 8.5 Hz); 6.55–6.53 (1H, multiplet).

2(5) 6-Chloroindoline

The procedure described in Example 1(5) was repeated, but using 232.0 mg (1.53 mmol) of 6-chloroindole [prepared as described in step (4) above] as the starting material, to obtain 212.7 mg (a quantitative yield) of the title compound as a brown oily substance.

¹H Nuclear Magnetic Resonance (200 MHz, CDCl₃) δ ppm: 6.99 (1H, doublet, J=7.7 Hz); 6.65 (1H, doublet of doublets, J=1.8 & 7.7 Hz); 6.59 (1H, doublet, J=1.8 Hz); 3.81 (1H, broad singlet); 3.58 (2H, triplet, J=8.4 Hz); 2.98 (2H, triplet, J=8.4 Hz).

2(6) 6-Chloro-1-(3-chloropropionyl)indoline 4.21 g (31.57 mmol×1.05 equivalents) of chloropropionyl chloride in 40 ml of acetone were added at room temperature to a solution of 4.85 g (31.57 mmol) of 6-chloroindoline [prepared as described in step (5) above] in acetone, and the mixture was heated under reflux for 2 hours. At the end of this time, the reaction mixture was poured into 10% w/v aqueous hydrochloric acid, and the solids which precipitated were collected by filtration. The filtrate was extracted with ethyl acetate and washed with water, after which it was dried over anhydrous magnesium sulfate. The mixture was filtered, and then the solvent was removed by distillation under reduced pressure, and the residue was dissolved in a small amount of ethyl acetate. Diisopropyl ether was added to the resulting solution, and the powder which precipitated was collected by filtration to obtain 4.00 g (yield: 51.9%) of the title compound as a pale yellow powder.

Mass Spectrum m/z: 243 (M⁺), 153, 152, 117. ¹H Nuclear Magnetic Resonance (200 MHz, CDCl₃) δ ppm: 8.28 (1H, doublet, J=1.9 Hz); 7.10 (1H, doublet, J=7.9 Hz); 7.00 (1H, doublet of doublets, J=1.9 & 7.9 Hz); 4.11 (2H, triplet, J=8.5 Hz); 3.91 (2H, triplet, J=6.8 Hz); 3.19 (2H, triplet, J=8.5 Hz); 2.91 (2H, triplet, J=6.8 Hz).

2(7) 7-Chloro-1,2,5,6tetrahydro-4H-pyrrolo[3,2,1-ij]quinolin-4-one (Compound No. 2)

2.82 g (11.54 mmol) of 6-chloro-1-(3-chloropropionyl)indoline [prepared as described in step (6) above] and 7.69 g (11.54 mmol×5 equivalents) of anhydrous aluminum chloride powder were heated at 120° C. for 3 hours. At the end of this time, the reaction mixture was poured into an ice-acid mixture consisting of 100 g of ice and 5 ml of 10% w/v aqueous hydrochloric acid. The mixture thus obtained was extracted with ethyl acetate, and the organic extract was dried over anhydrous magnesium sulfate. The mixture was filtered, and then the crude title compound obtained by distilling off the solvent under reduced pressure was purified by silica gel column chromatography, using a 2:1 by volume mixture of hexane and ethyl acetate as the eluent, followed by recrystallization (from a mixture of ethyl acetate and hexane), to give 1.14 g (yield: 47.6%) of the title compound as crystals, melting at 88°–91° C.

Mass Spectrum m/z: 209 (M⁺+2), 207 (M⁺), 178, 172, 164, 144, 130. ¹H Nuclear Magnetic Resonance (200 MHz, CDCl₃) δ ppm: 7.00 (1H, doublet, J=8.1 Hz); 6.93 (1H, doublet, J=8.1 Hz); 4.09 (2H, triplet, J=8.3 Hz); 3.15 (2H, triplet, J=8.3 Hz); 3.03 (2H, triplet, J=7.8 Hz); 2.70 (2H, triplet, J=7.8 Hz).

EXAMPLE 3

7,9-Difluoro-1,2,5,6-tetrahydro-4H-pyrrolo[3,2,1-i,j]quinolin-4-one (Compound No. 39)

3(1) 4,6-Difluoroindole

A solution of 1 g (6.29 mmol) of 3,5-difluoro-1-nitrobenzene in 27 ml of tetrahydrofuran was cooled to −65° C., and then 18.9 ml of a 1.01 mol/liter solution of vinylmagnesium bromide (18.71 mmol) in tetrahydrofuran was added dropwise to the cooled solution, while maintaining the internal temperature at −40° C. or lower. The mixture was then maintained at the same temperature for 30 minutes after completion of the addition. At the end of this time, an aqueous solution of ammonium chloride was added to the mixture to decompose excess vinylmagnesium bromide, and the mixture was then extracted with diethyl ether. The extract was washed with water and then with a saturated aqueous solution of sodium chloride, after which it was dried over anhydrous magnesium sulfate. The mixture was filtered, and then the crude title compound obtained by distilling off the solvent under reduced pressure was purified by silica gel column chromatography, using a 3:1 by volume mixture of hexane and ethyl acetate as the eluent, to give 134.3 mg (yield: 14.0%) of the title compound as an oily substance.

¹H Nuclear Magnetic Resonance (200 MHz, CDCl₃) δ ppm: 8.34 (1H, broad singlet); 7.19–7.14 (1H, multiplet); 6.90 (1H, doublet of doublets, J=1.4 & 8.5 Hz); 6.69–6.57 (2H, multiplet).

3(2) 4,6-Difluoroindoline

The procedure described in Example 1(5) was repeated, but using 134.3 mg (0.88 mmol) of 4,6-difluoroindole [prepared as described in step (1) above] as the starting material, to obtain 84.3 mg (yield: 62.0%) as a brown oily substance.

¹H Nuclear Magnetic Resonance (200 MHz, CDCl₃) δ ppm: 6.17–6.07 (2H, multiplet); 3.92 (1H, broad singlet); 3.64 (2H, triplet, J=8.4 Hz); 3.01 (2H, triplet, J=8.4 Hz).

3(3) 1-(3-Chloropropionyl)-4,6-difluoroindoline

The procedure described in Example 1(6) was repeated, but using 84.3 mg (0.54 mmol) of 4,6-difluoroindoline [prepared as described in step (2) above] as the starting material, to obtain 60.4 mg (yield: 45.3%) of the title compound as a black amorphous substance.

Mass Spectrum m/z: 245 (M⁺), 155, 154, 127. ¹H Nuclear Magnetic Resonance (200 MHz, CDCl₃) δ ppm: 7.81 (1H, doublet, J=9.2 Hz); 6.51 (1H, doublet of triplets, J=2.2 & 9.2 Hz); 4.16 (2H, triplet, J=8.3 Hz); 3.90 (2H, triplet, J=6.7 Hz); 3.20 (2H, triplet, J=8.3 Hz); 2.91 (2H, triplet, J=6.7 Hz).

3(4) 7,9-Difluoro-1,2,5,6tetrahydro-4H-pyrrolo[3,2,1-i,j]quinolin-4-one (Compound No. 39)

The procedure described in Example 1(7) was repeated, but using 60.4 mg (0.25 mmol) of 1-(3-chloropropionyl)-4,6-difluoroindoline [prepared as described in step (3) above] as the starting material, to obtain 10.1 mg (yield: 19.6%) of the title compound as an amorphous substance.

Mass Spectrum m/z: 209 (M⁺), 180, 166, 153. ¹H Nuclear Magnetic Resonance (200 MHz, CDCl₃) δ ppm: 6.39 (1H, triplet, J=9.5 Hz); 4.13 (2H, triplet, J=8.4 Hz 3.16 (2H, triplet, J=8.4 Hz); 2.94 (2H, triplet, J=7.7 Hz); 2.67 (2H, triplet, J=7.7 Hz).

EXAMPLE 4

7-Methyl-1,2,5,6-tetrahydro-4H-pyrrolo[3,2,1-ij]quinolin-4-one (Compound No. 5)

4(1) 6-Methylindoline

The procedure described in Example 1(5) was repeated, but using 847.2 mg (6.46 mmol) of 6-methylindole as the starting material, to obtain 860.5 mg (a quantitative yield) of the title compound as a pale yellow oily substance.

Mass Spectrum m/z: 133 (M⁺), 132, 118, 117. ¹H Nuclear Magnetic Resonance (200 MHz, CDCl₃) δ ppm: 7.01 (1H, doublet, J=7.7 Hz); 6.54 (1H, doublet, J=7.7 Hz); 6.51 (1H, singlet); 3.55 (2H, triplet, J=8.4 Hz); 3.00 (2H, triplet, J=8.4 Hz); 2.28 (3H, singlet).

4(2) 1-(3-Chloropropionyl)-6-methylindoline

The procedure described in Example 1(6) was repeated, but using 860.5 mg (6.46 mmol) of 6-methylindoline

[prepared as described in step (1) above] as the starting material, to obtain 1.315 g (yield: 91%) of the title compound as a white powder.

Mass Spectrum m/z: 223 (M$^+$), 149, 133, 132, 117. $^1$H Nuclear Magnetic Resonance (200 MHz, CDCl$_3$) δ ppm: 8.10 (1H, singlet); 7.07 (1H, doublet, J=7.6 Hz); 6.86 (1H, doublet, J=7.6 Hz); 4.07 (2H, triplet, J=8.3 Hz); 3.92 (2H, triplet, J=6.8 Hz); 3.17 (2H, triplet, J=8.3 Hz); 2.91 (2H, triplet, J=6.8 Hz); 2.34 (3H, singlet).

4(3) 7-Methyl-1,2,5,6-tetrahydro-4H-pyrrolo[3,2,1-ij]quinolin-4-one (Compound No. 5)

The procedure described in Example 1(7) was repeated, but using 1.292 g (5.77 mmol) of 1-(3-chloropropionyl)-6-methylindoline [prepared as described in step (2) above] as the starting material, to obtain 205 mg (yield: 19%) of the title compound as a pale yellow amorphous substance.

Mass Spectrum m/z: 187 (M$^+$), 172, 158, 144, 130. $^1$H Nuclear Magnetic Resonance (200 MHz, CDCl$_3$) δ ppm: 6.99 (1H, doublet, J=7.7 Hz); 6.80 (1H, doublet, J=7.7 Hz); 4.08 (2H, triplet, J=8.3 Hz); 3.16 (2H, triplet, J=8.3 Hz); 2.93 (2H, triplet, J=7.6 Hz); 2.71 (2H, triplet, J=7.6 Hz); 2.26 (3H, singlet).

EXAMPLE 5

7-Methoxy-1,2,5,6-tetrahydro-4H-pyrrolo[3,2,1-ij]quinolin-4-one (Compound No. 17)

5(1) 6-Methoxyindoline

The procedure described in Example 1(5) was repeated, but using 1.00 g (6.85 mmol) of 6-methoxyindole as the starting material, to obtain 0.95 g (yield: 93.0%) of the title compound as a pale yellow oily substance.

Mass Spectrum m/z: 149 (M$^+$), 148, 134, 133, 117. $^1$H Nuclear Magnetic Resonance (200 MHz, CDCl$_3$) δ ppm: 7.05 (1H, doublet, J=7.1 Hz); 6.31 (1H, doublet, J=7.1 Hz); 6.29 (1H, singlet); 3.80 (3H, singlet); 3.60 (2H, triplet, J=8.2 Hz); 3.01 (2H, triplet, J=8.2 Hz).

5(2) 1-(3-Chloropropionyl)-6-methoxyindoline

The procedure described in Example 1(6) was repeated, but using 948.6 mg (6.36 mmol) of 6-methoxyindoline [prepared as described in step (1) above] as the starting material, to obtain 1.274 g (yield: 83.6%) of the title compound as a white powder.

Mass Spectrum m/z: 239 (M$^+$), 149, 148, 133, 121, 117. $^1$H Nuclear Magnetic Resonance (200 MHz, CDCl$_3$) δ ppm: 8.03 (1H, doublet, J=2.4 Hz); 7.16 (1H, doublet, J=8.2 Hz); 6.71 (1H, doublet of doublets, J=2.4 & 8.2 Hz); 4.20 (2H, triplet, J=8.4 Hz); 4.02 (2H, triplet, J=6.8 Hz); 3.91 (3H, singlet); 3.25 (2H, triplet, J=8.4 Hz); 3.02 (2H, triplet, J=6.8 Hz).

5(3) 7-Hydroxy-1,2,5,6-tetrahydro-4H-pyrrolo[3,2,1-ij]quinolinone-4-one

A mixture of 577.1 mg (2.41 mmol) of 1-(3-chloropropionyl)-6-methoxyindoline [prepared as described in step (2) above] and 1.61 g (12.04 mmol) of anhydrous aluminum chloride powder was heated at 120° C. (bath temperature: 160° C.) for 3 hours. At the end of this time, the reaction mixture was treated in the same manner as described in Example 1(7) to obtain 349.1 mg (yield: 76.6%) of the title compound as a white powder, melting at 233°–242° C.

Mass Spectrum m/z: 189 (M$^+$), 167, 160, 147, 130. $^1$H Nuclear Magnetic Resonance (200 MHz, CDCl$_3$) δ ppm: 6.89 (1H, doublet, J=8.1 Hz); 6.44 (1H, doublet, J=8.1 Hz); 4.01 (2H, triplet, J=8.3 Hz); 3.08 (1H, triplet, J=8.3 Hz); 2.91 (2H, triplet, J=7.8 Hz); 2.62 (2H, triplet, J=7.8 Hz).

5(4) 7-Methoxy-1,2,5,6-tetrahydro-4H-pyrrolo[3,2,1-ij]quinolin-4-one (Compound No. 17)

73.3 mg (0.53 mmol) of potassium carbonate and 48 μl (0.77 mmol) of methyl iodide were added to a solution of 98.4 mg (0.52 mmol) of 7-hydroxy-1,2,5,6-tetrahydro-4H-pyrrolo[3,2,1-ij]quinolin-4-one [prepared as described in step (3) above] in 7 ml of acetone, and then the mixture was stirred at 60° to 70° C. for 8 hours. At the end of this time, the acetone was removed by distillation under reduced pressure, and water was added to the residue. The mixture was then extracted with ethyl acetate. The organic extract was washed with water and with a saturated aqueous solution of sodium chloride, in that order, after which it was dried over anhydrous magnesium sulfate. The mixture was filtered, and then the solvent was removed by distillation under reduced pressure. The crude title compound thus obtained was purified by preparative thin layer chromatography over silica gel, using a 1:8 by volume mixture of hexane and ethyl acetate as developing solvent [plate of thickness of 0.5 mm, 20 cm×20 cm, 4 sheets], to obtain 36.7 mg (yield: 34.7%) of the title compound as a pale yellow powder, melting at 101°–114° C.

Mass Spectrum m/z: 203 (M$^+$), 188, 172, 160, 146, 130. $^1$H Nuclear Magnetic Resonance (200 MHz, CDCl$_3$) δ ppm: 7.00 (1H, doublet, J=8.2 Hz); 6.47 (1H, doublet, J=8.2 Hz); 4.07 (2H, triplet, J=8.3 Hz); 3.82 (3H, singlet); 3.11 (2H, triplet, J=8.3 Hz); 2.92 (2H, triplet, J=7.9 Hz); 2.65 (2H, triplet, J=7.9 Hz).

EXAMPLE 6

7-Difluoromethoxy-1,2,5,6-tetrahydro-4H-pyrrolo[3,2,1-ij]quinolin-4-one (Compound No. 37)

128.9 mg (2.15 mmol) of sodium hydride (as a 40% w/w dispersion in mineral oil) were added at 0° C. to a solution of 339.1 mg (1.79 mmol) of 7-hydroxy-1,2,5,6-tetrahydro-4H-pyrrolo[3,2,1-ij]quinolin-4-one [prepared as described in Example 5(3)] in 9.1 ml of dimethylformamide. Chlorodifluoromethane gas was blown into the resulting mixture through a tube, while ice-cooling, for a period of 20 minutes. At the end of this time, the mixture was poured into ice-water and extracted with ethyl acetate. The organic extract was washed with water and with a saturated aqueous solution of sodium chloride, in that order, and dried over anhydrous magnesium sulfate. It was then filtered, and the solvent was removed by distillation under reduced pressure. The crude title compound thus obtained was purified over silica gel column chromatography, using a 1:2 by volume mixture of hexane and ethyl acetate as the eluent, to give 151.8 mg (yield: 35.4%) of the title compound as a pale yellow powder, melting at 98°–108° C.

Mass Spectrum m/z: 239 (M$^+$), 167, 149, 13. $^1$H Nuclear Magnetic Resonance (200 MHz, CDCl$_3$) δ ppm: 7.03 (1H, doublet, J=8.1 Hz); 6.70 (1H, doublet, J=8.1 Hz); 6.49 (1H, triplet, J=73.9 Hz); 4.10 (2H, triplet, J=8.4 Hz); 3.16 (2H, triplet, J=8.4 Hz); 2.99 (2H, triplet, J=7.8 Hz); 2.66 (2H, triplet, J=7.8 Hz).

EXAMPLE 7

7-Methoxy-6-methyl-1,2-dihydro-4H-pyrrolo[3,2,1-ij]quinolin-4-one (Compound No. 269)

7(1) 1-(1,3-Dioxobutyl-6-methoxyindoline

A solution of 305.8 mg (3.64 mmol) of diketene in 3.4 ml of dichloroethane was added at room temperature to a solution of 506.7 mg (3.4 mmol) of 6-methoxyindoline [prepared as described in Example 5(1)] in 3.4 ml of dichloroethane, and the resulting mixture was heated under reflux for 7 hours. At the end of this time, the solvent was removed by distillation under reduced pressure, and the residue was purified by silica gel column chromatography, using a 2:1 by volume mixture of hexane and ethyl acetate as the eluent, to give 720 mg (yield: 90.9%) of the title compound as a brown oily substance. The title compound was a mixture of the enol form and the keto form in a proportion of about 1:1.

Mass Spectrum m/z: 233 (M$^+$), 149, 148, 133, 118, 117. $^1$H Nuclear Magnetic Resonance (200 MHz, CDCl$_3$) δ ppm: 7.90 (doublet, J=2.4 Hz); 7.26 (singlet); 7.05 (doublet, J=8.2 Hz); 6.59 (doublet of triplets, J=2.4 & 8.2 Hz); 5.11 (broad singlet); 4.07 (triplet, J=8.3 Hz); 3.82 (singlet); 3.81 (singlet); 3.63 (singlet); 3.13 (triplet, J=8.3 Hz); 2.35 (singlet); 2.02 (singlet).

7(2) 7-Methoxy-6-methyl-1,2-dihydro-4H-pyrrolo[3,2,1-ij]quinolin-4-one (Compound No. 269)

A mixture of 695.7 mg (2.98 mmol) of 1-(1,3-dioxobutyl)-6-methoxy-indoline [prepared as described in step (1) above] and 0.9 ml of concentrated sulfuric acid was heated in an oil bath maintained at 70° C. The temperature of the mixture was raised to 100° C., and the reaction was finished after 15 minutes. At the end of this time, ice was added to the reaction mixture and the solids which precipitated were collected by filtration. They were then washed with water and air-dried. The residue was dissolved in methanol, and the resulting methanolic solution was concentrated by evaporation under reduced pressure, to obtain 565.6 mg (yield: 88.1%) of the title compound as a white powder, melting at 148°–154° C.

Mass Spectrum m/z: 215 (M$^+$), 200, 184, 172. $^1$H Nuclear Magnetic Resonance (200 MHz, CDCl$_3$) δ ppm: 7.30 (1H, doublet of doublets, J=1.3 & 8.1 Hz); 6.70 (1H, doublet, J=8.1 Hz); 6.29 (1H, doublet, J=1.3 Hz); 4.32 (2H, triplet, J=8.1 Hz); 3.89 (3H, singlet); 3.30 (2H, triplet, J=8.1 Hz); 2.61 (3H, singlet).

EXAMPLE 8

7-Difluoromethoxy-6-methyl-1,2-dihydro-4H-pyrrolo[3,2,1-ij]quinolin-4-one (Compound No. 289)

8(1) 7-Hydroxy-6-methyl-1,2-dihydro-4H-pyrrolo[3,2,1-ij]quinolin-4-one

A solution of 215.6 mg (1.00 mmol) of 7-methoxy-6-methyl-1,2-dihydro-4H-pyrrolo[3,2,1-ij]quinolin-4-one (Compound No. 269) [prepared as described in Example 7(2)] in 10 ml of methylene chloride was cooled to −78° C. using dry ice-acetone, and 1.7 ml of a 1.0M solution of boron tribromide (1.7 mmol) in methylene chloride was added to the cooled solution. The mixture was stirred at room temperature overnight, after which it was poured into ice-water. The solids which precipitated were collected by filtration and washed with water, after which they were air-dried, to obtain 130.9 mg (yield: 64.9%) of the title compound as a powder.

Mass Spectrum m/z: 201 (M$^+$), 184, 173, 172, 158. $^1$H Nuclear Magnetic Resonance (200 MHz, CDCl$_3$) δ ppm: 10.04 (1H, singlet); 7.14 (1H, doublet, J=7.9 Hz); 6.52 (1H, doublet, J=7.9 Hz); 6.18 (1H, singlet); 4.18 (2H, triplet, J=7.0 Hz); 3.20 (2H, triplet, J=7.0 Hz); 2.57 (3H, singlet).

8(2) 7-Difluoromethoxy-6methyl-1,2-dihydro-4H-pyrrolo[3,2,1-ij]quinolin-4-one (Compound No.289)

The procedure described in Example 6 was repeated, but using 84.2 mg (0.42 mmol) of 7-hydroxy-6-methyl-1,2-dihydro-4H-pyrrolo[3,2,1-ij]quinolin-4-one [prepared as described in step (1) above] as the starting material, to obtain 10.3 mg (yield: 9.8%) of the title compound as a white powder, melting at 148°–154° C.

Mass Spectrum m/z: 251 (M$^+$), 200, 184, 172, 154. $^1$H Nuclear Magnetic Resonance (200 MHz, CDCl$_3$) δ ppm: 7.24 (1H, doublet, J=7.7 Hz); 6.81 (1H, doublet, J=7.7 Hz); 6.57 (1H, triplet, J=73.5 Hz); 6.47 (1H, singlet); 4.42 (2H, triplet, J=8.2 Hz); 3.37 (2H, triplet, J=8.2 Hz); 2.61 (3H, singlet).

EXAMPLE 9

7-Methoxy-6-methyl-1,2,5,6-tetrahydro-4H-pyrrolo[3,2,1-ij]quinolin4-one (Compound No. 69)

A solution of 283 mg (1.32 mmol) of 7-methoxy-6-methyl-1,2-dihydro-4H-pyrrolo[3,2,1-ij]quinolin-4-one (Compound No. 269) [prepared as described in Example 7(2)] and 84.7 mg (29.57% by weight) of platinum (IV) oxide in 19 ml of isopropyl alcohol was reduced by Paal's catalytic reduction apparatus [which is described in Shin Jikken Kagaku Koza, 15 (II), p. 412 (1977)]. At the end of this time, the catalyst was separated by filtration, and the solvent was removed by distillation under reduced pressure. The residue was then purified by preparative thin layer chromatography on silica gel, using ethyl acetate as the developing solvent [silica gel plate, thickness: 0.5 mm, 20 cm×20 cm, 4 sheets], to obtain 112.6 mg (yield: 38.9%) of the title compound as a powder, melting at 105°–109° C.

Mass Spectrum m/z: 217 (M$^+$), 202, 187, 174. $^1$H Nuclear Magnetic Resonance (200 MHz, CDCl$_3$) δ ppm: 7.01 (1H, doublet, J=8.2 Hz); 6.54 (1H, doublet, J=8.2 Hz); 4.06–3.88 (2H, multiplet); 3.83 (3H, singlet); 3.34 (1H, doublet of triplets, J=1.6 & 7.0 Hz); 3.14–3.03 (2H, multiplet); 2.78 (1H, doublet of doublets, J=7.0 & 18.7 Hz); 2.31 (1H, doublet of doublets, J=1.6 & 18.7 Hz); 1.08 (3H, doublet, J=7.0 Hz).

EXAMPLE 10

7-Fluoro-6-methyl-1,2-dihydro4H-pyrrolo[3,2,1-ij]quinolin-4-one (Compound No. 253)

10(1) 1-(1,3-Dioxobutyl)-6-fluoroindoline

The procedure described in Example 7 (1) was repeated, but using 101.2 mg (0.738 mmol) of 6-fluoroindoline [prepared as described in Example 1(5)] as the starting material, to obtain 172.6 mg (a quantitative yield) of the crude title compound as a brown oily substance. The product was a mixture of the keto form and the enol form of the title compound.

Mass Spectrum m/z: 221 (M$^+$), 137, 136, 125, 109. $^1$H Nuclear Magnetic Resonance (200 MHz, CDCl$_3$) δ ppm: 7.97 (doublet of doublets, J=2.2 & 10.6 Hz); 7.13–7.06 (multiplet); 6.74 (doublet of triplets, J=2.2 & 8.5 Hz); 5.11

(broad singlet); 4.10 (triplet, J=8.3 Hz); 4.06 (triplet, J=8.3 Hz); 3.73 (singlet); 3.64 (singlet); 3.15 (triplet, J=8.5 Hz); 2.35 (singlet); 2.02 (singlet).

10(2) 7-Fluoro-6-methyl-1,2-dihydro-4H-pyrrolo[3,2,1-ij] quinolin4-one (Compound No. 253)

The procedure described in Example 7 (2) was repeated, but using 162.6 mg (0.73 mmol) of 1-(1,3-dioxobutyl)-6-fluoroindoline [prepared as described in step (1) above] as the starting material, to obtain 36.8 mg (yield: 24.6%) of the title compound as a pale yellow powder, melting at 172°–198° C.

Mass Spectrum m/z: 203 ($M^+$), 202, 174, 146. $^1$H Nuclear Magnetic Resonance (200 MHz, $CDCl_3$) δ ppm: 7.31 (1H, doublet of doublets, J=4.4 & 8.0 Hz); 6.81 (1H, doublet of doublets, J=8.0 & 12.7 Hz); 6.31 (1H, doublet, J=1.1 Hz); 4.30 (2H, triplet, J=8.2 Hz); 3.35 (2H, triplet, J=8.2 Hz); 2.52 (3H, doublet of doublets, J=1.1 & 4.6 Hz).

EXAMPLE 11

7-Fluoro-1,2,5,6-tetrahydro-4H-pyrrolo[3,2,1-ij] guinolin-4one (Compound No. 1)

236 g (1.77 mol) of anhydrous aluminum chloride powder were added to 200 g (0.88 mol) of 1-(3-chloropropionyl)-6-fluoroindoline [prepared as described in Example 1(6)], and the mixture was stirred while heating at an oil bath temperature of 150° C. for 2 hours. A further 12 g (0.09 mol) of anhydrous aluminum chloride powder was then added to the reaction mixture at the same temperature, and the mixture was stirred for 40 minutes. Another 12 g (0.09 mol) of anhydrous aluminum chloride powder was then added to the reaction mixture, and the mixture was stirred for 1.5 hours. At the end of this time, the reaction mixture was cooled to room temperature, and 2 liters of ice-water were poured into the reaction mixture in an ice bath. 0.8 liter of ethyl acetate was then added, and the mixture was vigorously stirred. The reaction mixture was then transferred into a separating funnel, and 2 liters of water and 0.7 liter ethyl acetate were added to extract the reaction mixture, and were separated into an aqueous phase and an organic phase (hereinafter "the first extract"). The first extract was washed three times, each time with 0.7 liter of water, and was then washed with 0.5 liter of a saturated aqueous solution of sodium hydrogencarbonate and with 0.4 liter of a saturated aqueous solution of sodium chloride, in that order. The aqueous sodium chloride washings were extracted with 1 liter of ethyl acetate. The aqueous sodium hydrogencarbonate washings were extracted with the resulting extract. The aqueous washings were extracted with the same extract. Finally, the aqueous phase was extracted with the same extract. The extract from the washings and the aqueous phase was washed three times, each time with 0.7 liter of water, and was then washed with 0.5 liter of a saturated aqueous solution of sodium hydrogencarbonate and with 0.4 liter of a saturated aqueous solution of sodium chloride, in that order. The resulting washed extract was combined with the washed first extract and dried over anhydrous sodium sulfate. The drying agent was filtered off, the filtrate was concentrated by evaporation under reduced pressure, which precipitated crystals. About 50 ml of a 1:3 by volume mixture of ethyl acetate and diisopropyl ether were added to these crystals, and the mixture was vigorously stirred to wash the crystals. The crystals were collected by filtration, washed with a solvent whose composition was gradually changed from a 1:3 by volume mixture of ethyl acetate and diisopropyl ether to only diisopropyl ether, and then dried to obtain 119.0 g (0.624 mol) of the title compound. The filtrate and the washing solution were combined and then concentrated by evaporation under reduced pressure, and the further crystals which precipitated were collected by filtration, and were then washed by the same procedure as described above to obtain a further 16.3 g (0.085 mol) of the title compound (total yield: 80%).

PREPARATION 1

6-Fluoroindole

This provides an alternative method of preparing the title compound, whose preparation is also described in Example 1(4).

17.3 ml (0.208 mol) of pyrrolidine and 28.0 ml (0.211 mol) of dimethylformamide dimethylacetal were added to a solution of 26.9 g (0.173 mol) of 4-fluoro-2-nitrotoluene in 119 ml of dimethyl formamide, and the mixture was heated with stirring at 105° C. for 6.5 hours. The resulting red reaction solution was cooled, and 736 ml of a 4M aqueous solution of ammonium acetate were added to the cooled solution, followed by the addition of 749 ml of dimethyl formamide. 617 ml of a 20% w/v aqueous solution of titanium trichloride were then added dropwise to the resulting mixture over a period of 1 hour. A 2.1N aqueous solution of sodium hydroxide was then added dropwise to the reaction solution to make it basic, and the mixture was extracted with ethyl acetate. The organic extract was washed with water and dried over anhydrous magnesium sulfate. It was then filtered and the solvent was removed by distillation under reduced pressure to obtain 21.35 g (yield: 91.1%) of the title compound as an amorphous substance. The Nuclear Magnetic Resonance data of the product were essentially the same as those of the product prepared as described in Example 1(4) and the product had a purity sufficient for it to be used for subsequent reactions in place of the product of Example 1(4).

PREPARATION 2

6-Fluoroindole

This provides another alternative method of preparing the title compound, whose preparation is also described in Example 1(4).

2(1) β-Pyrrolidino-4-fluoro-2-nitrostyrene 10.7 ml (0.13 mol) of pyrrolidine and 17.3 ml (0.13 mol) of dimethylformamide dimethylacetal were added to a solution of 16.6 g (0.107 mol) of 4-fluoro-2-nitrotoluene in 74 ml of dimethyl formamide, and the mixture was heated with stirring at 105° C. for 6.5 hours. At the end of this time, the reaction solution was diluted with water and extracted with diethyl ether. The organic extract was washed with water and dried over anhydrous magnesium sulfate. The mixture was filtered, and then the solvent was removed by distillation under reduced pressure to obtain 25.00 g (yield: 98.9%) of the title compound as a red oily substance.

Mass Spectrum m/z: 236 ($M^+$), 219, 188, 177, 166, 161, 148, 138, 120, 112. $^1$H Nuclear Magnetic Resonance (200 MHz, $CDCl_3$) δ ppm: 7.61 (1H, doublet of doublets, J=2.8 & 9.0 Hz); 7.42 (1H, doublet of doublets, J=5.4 & 9.0 Hz); 7.15 (1H, doublet, J=13.4 Hz); 7.15–7.05 (1H, multiplet); 5.84 (1H, doublet, J=13.4 Hz); 3.35–3.29 (4H, multiplet); 1.99–1.92 (4H, multiplet).

2(2) 6-Fluoroindole

A solution of 24.90 g (0.105 mol) of β-pyrrolidino-4-fluoro-2-nitrostyrene [prepared as described in step (1)

above] in 150 ml of ethyl acetate was reduced using Paal's catalytic reduction apparatus and 1.8 g of 10% w/w palladium-on-charcoal as a catalyst. The catalyst was separated from the reaction mixture by filtration and the filtrate was concentrated by evaporation under reduced pressure to obtain 13.23 g (yield: 92.9%) of the title compound as a blackish brown amorphous substance. The Nuclear Magnetic Resonance data of the product were essentially the same as those of the product prepared as described in Preparation 1 and the purity of the product was substantially the same as that of the product of Preparation 1.

PREPARATION 3

1-(3-Chloropropionyl)-6-fluoroindoline

This provides an alternative method of preparing the title compound, whose preparation is also described in Example 1(6).

424 ml (3.35 mol) of a boron trifluoride-diethyl ether complex were added dropwise at 0° C. over a period of 40 minutes to 1.5 liters of a suspension of 106 g (2.52 mol) of sodium borohydride (purity 90%) in tetrahydrofuran, and the mixture was stirred at room temperature for 1 hour. At the end of this time, 194 g (1.28 mol) of 6-fluorooxindole was added at 0° C. to the reaction mixture, and the mixture was heated under reflux for 84 hours. The reaction mixture was then cooled to 0° C., after which 1 liter of 6N aqueous hydrochloric acid was added dropwise over a period of 30 minutes. The resulting mixture was heated under reflux for 2 hours, after which it was concentrated by distillation at atmospheric pressure until the volume of the reaction mixture was reduced to about 1 liter. About 400 g of sodium hydroxide was added to the reaction mixture at 0° C. over a period of 1 hour to adjust the pH to a value of at least 14, and then the mixture was filtered. The filtrate was extracted with 1 liter of ethyl acetate and the organic extract was dried over anhydrous sodium sulfate. The mixture was filtered, and then the solvent was removed from the filtrate by distillation under reduced pressure to obtain 370 g of a crude product containing 6-fluoroindoline.

This crude product was dissolved in 1 liter of acetone, and 125 ml of 3-chloropropionyl chloride was added dropwise to the resulting solution at 0° C. over a period of 50 minutes, after which the mixture was heated under reflux for 40 minutes. The reaction mixture was then cooled to room temperature and concentrated by evaporation under reduced pressure until the volume of the mixture was reduced to about 400 ml. 500 ml of water and 100 ml of acetone were added to the reaction mixture, and the precipitated crystals were collected by filtration. The crystals were washed with water and then air-dried. The crystals thus obtained were washed with a 2:3 by volume mixture of ethyl acetate and hexane and then with hexane and dried to obtain 158 g (yield: 54%) of the title compound as pale yellow crystals.

PREPARATION 4

6-Nitroindoline 5.96 g (50 mmol) of indoline were dissolved in 25 ml of concentrated sulfuric acid, and a mixture of 3.75 ml of concentrated nitric acid (61%) and 25 ml of concentrated sulfuric acid was added to the solution while ice-cooling so that the internal temperature was maintained at 10° C. or lower. The mixture was then stirred while ice-cooling for 2 hours. At the end of this time, a 75% w/v aqueous solution of sodium hydroxide was added to the reaction mixture while ice-cooling to neutralize the reaction mixture, while maintaining the internal temperature at 60° C. or lower. The mixture was then extracted with ethyl acetate. The organic extract was dried over anhydrous magnesium sulfate and, after filtration, the solvent was removed from the filtrate by distillation under reduced pressure to obtain 7.8 g (47.5 mmol) of the title compound as crystals, melting at 65°–68° C. (yield: 95%).

$^1$H Nuclear Magnetic Resonance (200 MHz, CDCl$_3$) δ ppm: 3.10 (2H, triplet, J=8.5 Hz); 3.69 (2H, triplet, J=8.5 Hz); 4.04 (1H, broad singlet); 7.15 (1H, doublet, J=8.1 Hz); 7.35 (1H, doublet, J=2.1 Hz); 7.56 (1H, doublet of doublets, J=2.1 & 8.1 Hz).

PREPARATION 5

1-(3-Chloropropionyl)6-nitroindoline 8.2 g (50 mmol) of 6-nitroindoline (prepared as described in Preparation 4) were dissolved in 100 ml of acetone, and 6.35 g (50 mmol) of 3-chloropropionyl chloride were added to the solution while ice-cooling, which resulted in the reaction mixture becoming a suspension. This suspension was stirred at room temperature for 1 hour, after which it was heated under reflux for 2 hours, and formed a solution. The resulting solution was cooled to room temperature, and then 10% w/v aqueous hydrochloric acid was added, and the precipitated crystals were collected by filtration. The crystals thus obtained were dried over phosphorous pentoxide in a desiccator under reduced pressure by means of a vacuum pump overnight to obtain 12.7 g (50 mmol) of the title compound as crystals, melting at 127°–128° C. (yield: 100%).

$^1$ H Nuclear Magnetic Resonance (200 MHz, CDCl$_3$) δ ppm: 2.95 (2H, triplet, J=6.7 Hz); 3.32 (2H, triplet, J=8.6 Hz); 3.93 (2H, triplet, J=6.7 Hz); 4.22 (2H, triplet, J=8.6 Hz); 7.30 (1H, doublet, J=8.2 Hz); 7.93 (1H, doublet of doublets, J=2.0 & 8.2 Hz); 9.03 (1H, doublet, J=2.0 Hz).

Mass Spectrum (m/z): 254 (M$^+$), 218, 164, 118.

PREPARATION 6

6-Amino-1-(3-chloropropionyl)indoline 1 g (4.4 mmol) of platinum oxide was suspended in 50 ml of ethanol, and a solution of 9.5 g (37.3 mmol) of 1-(3-chloropropionyl)-6-nitroindoline (prepared as described in Preparation 5) (4), which was obtained by the above reaction, in a mixture of 200 ml of ethanol and 100 ml of ethyl acetate was added to the suspension. The reaction mixture was then transferred to a Paar's reaction device and hydrogen gas was introduced at 4 to 5 atmospheres. Hydrogenation was carried out at room temperature. The reaction mixture vigorously absorbed the hydrogen gas during the initial 1 hour. The reaction was carried out for a further 4 hours until the reaction mixture no longer absorbed the hydrogen gas completely. The reaction mixture was then filtered using a Celite (trade mark) filter aid and washed five times with hot acetonitrile. The washing solutions were combined and the solvent was removed by distillation under reduced pressure to obtain 7.88 g (35 mmol) of the title compound as crystals, melting at 158°–159° C. (yield: 94%).

$^1$H Nuclear Magnetic Resonance (200 MHz, in hexadeuterated dimethyl sulfoxide) δ ppm: 2.96 (2H, triplet, J=6.6 Hz); 2.96 (2H, triplet, J=8.4 Hz); 3.87 (2H, triplet, J=6.6 Hz); 4.04 (2H, triplet, J=8.4 Hz); 4.98 (2H, broad singlet); 6.23 (1H, doublet of doublets, J=2.0 & 8.1 Hz); 6.86 (1H, doublet, J=8.1 Hz); 7.47 (1H, doublet, J=2.0 Hz). Mass Spectrum (m/z): 224 (M$^+$), 188, 134, 106.

PREPARATION 7

1-(3-Chloropropionyl)-6-fluoroindoline 225 mg (1.0 mmol) of 6-amino-1-(3-chloropropionyl) indoline (prepared as described in Preparation 6) were dissolved in a Teflon (trade mark) vessel, (5) obtained in the above reaction in 3 ml of 70% hydrogen fluoride-pyridine, while ice-cooling, and then the solution was diluted with 1.2 ml of pyridine. The mixture was then stirred at room temperature for 30 minutes. At the end of this time, the reaction mixture was ice-cooled again, and 83 mg (1.2 mmol) of sodium nitrite were added while maintaining the internal temperature at 10° C. or lower. The mixture was then stirred at room temperature for 30 minutes and at 70° C. for 4 hours. The reaction mixture was then poured into ice and extracted with ethyl acetate. The organic extract was washed with a saturated aqueous solution of sodium chloride and dried over anhydrous magnesium sulfate. The mixture was filtered, and the solvent was removed from the filtrate by distillation under reduced pressure. The residue thus obtained was subjected to preparative thin layer silica gel chromatography, using a 7:3 by volume mixture of hexane and ethyl acetate as the developing solvent, to obtain 160 mg (0.7 mmol) of the title compound as crystals, melting at 117°–119° C. from a band of Rf=0.4 (yield: 70%).

$^1$H Nuclear Magnetic Resonance (200 MHz, CDCl$_3$) δ ppm: 2.89 (2H, triplet, J=6.8 Hz); 3.16 (2H, triplet, J=8.5 Hz); 3.89 (2H, triplet, J=6.8 Hz); 4.10 (2H, triplet, J=8.5 Hz); 6.71 (1H, doublet of triplets, J=2.4 & 8.5 Hz); 7.09 (1H, doublet of doublets, J=5.6 & 8.5 Hz); 7.97 (1H, doublet of doublets, J=2.4 & 10.5 Hz). Mass Spectrum (m/z): 227 (M$^+$), 137, 136.

PREPARATION 8

1-(3-Chloropropionyl)-6-fluoroindoline 400 mg (1.8 mmol) of 6-amino-1-(3-chloropropionyl) indoline (prepared as described in Preparation 6) were dissolved in 5 ml of water and 2.5 ml of concentrated aqueous hydrochloric acid, and a solution of 140 mg (2.0 mmol) of sodium nitrite in 1 ml of water was added to the solution while ice-cooling so that the internal temperature was maintained at 10° C. or lower. The mixture was then stirred while ice-cooling for 30 minutes. At the end of this time, 730 mg (3.0 mmol) of fluoboric acid (as a 42% w/v aqueous solution) were added to the mixture while ice-cooling and the mixture was stirred at the same temperature for 1 hour. The crystals which precipitated were then collected by filtration and dried over phosphorous pentoxide in a desiccator under reduced pressure by means of a vacuum pump overnight. They were then dissolved in 10 ml of dodecane, and the mixture was heated to 180° C., and then stirred for 1 hour. At the end of this time, the reaction solution was cooled to room temperature, and then poured into ice. The mixture was then extracted with ethyl acetate. The organic extract was washed with a saturated aqueous solution of sodium chloride and dried over anhydrous magnesium sulfate. The mixture was filtered, and then the solvent was removed by distillation under reduced pressure. The resulting residue was purified by silica gel column chromatography, using a 4:1 by volume mixture of hexane and ethyl acetate as the eluent, to give 160 mg (0.7 mmol) of the title compound as crystals (yield: 39%).

PREPARATION 9

1-(3-Chloropropionyl)-6-fluoroindoline 260 mg (2.2 mmol) of 6-amino-1-(3-chloropropionyl) indoline (prepared as described in Preparation 6) were dissolved in 10 ml of methylene chloride, and 450 mg (2.0 mmol) of nitrosonium tetrafluoroborate were added to the resulting solution while ice-cooling so that the internal temperature was maintained at 10° C. or lower. The mixture was then stirred while ice-cooling for 30 minutes. At the end of this time, 10 ml of 1,2-dichlorobenzene were added to the mixture, and the mixture was stirred at 90° C. for 1 hour. The solvent was then removed from the reaction mixture by distillation under reduced pressure and the resulting residue was purified by silica gel column chromatography, using a 4:1 by volume mixture of hexane and ethyl acetate as the eluent, to give 97 mg (0.39 mmol) of the title compound as crystals (yield: 20%).

PREPARATION 10

1-(3-Chloropropionyl)-6-fluoroindoline

10(1) 1-(3-Chloropropionyl)indoline-diazonium tetrafluoroborate 1.12 g (5.0 mmol) of 6-amino-1-(3-chloropropionyl) indoline (prepared as described in Preparation 6) were suspended in 80 ml of 6N aqueous hydrochloric acid, and a solution of 380 mg (5.5 mmol) of sodium nitrite in 5 ml of water were added to the suspension while ice-cooling so that the internal temperature was maintained at 10° C. or lower. The mixture was then stirred while ice-cooling for 30 minutes. At the end of this time, 2.0 g (8.4 mmol) of fluoboric acid (as a 42% w/v aqueous solution) were added to the mixture, and the mixture was stirred at the same temperature for 1 hour. The reaction mixture was then concentrated by evaporation under reduced pressure to obtain 2.1 g of a solid, which was crude 1-(3-chloropropionyl)indoline-6-diazonium tetrafluoroborate.

$^1$H Nuclear Magnetic Resonance (200 MHz, CDCl$_3$) δ ppm: 3.10 (2H, triplet, J=6.3 Hz); 3.45 (2H, triplet, J=8.6 Hz); 3.91 (2H, triplet, J=6.3 Hz); 4.28 (2H, triplet, J=8.6 Hz); 7.72 (1H, doublet, J=8.2 Hz); 8.37 (1H, doublet of doublets, J=2.0 & 8.2 Hz); 9.14 (1H, doublet, J=2.0 Hz).

10(2) 1-(3-Chloropropionyl)-6-fluoroindoline 320 mg of crude 1-(3-chloropropionyl)indoline-6-diazonium tetrafluoroborate [prepared as described in step (1) above] were heated to 80° C. in the absence of a solvent, which caused it to foam. The resulting mixture was extracted with 50 ml of ethyl acetate and washed with 50 ml of water, after which it was dried over anhydrous magnesium sulfate. The mixture was filtered, and then the solvent was removed from the filtrate by distillation under reduced pressure. The resulting residue was purified by silica gel column chromatography, using a 4:1 by volume mixture of hexane and ethyl acetate as the eluent, to give 50 mg (0.22 mmol) of the title compound (yield: 29% in two steps).

10(3) 1-(3-Chloropropionyl)-6-fluoroindoline 320 mg of crude 1-(3-chloropropionyl)indoline-6-diazonium tetrafluoroborate [prepared as described in step (1) above] were suspended in 10 ml of heptane, and the suspension was heated under reflux for 1 hour. The resulting mixture was cooled to room temperature, and then the reaction product was poured into ice, extracted with 50 ml of ethyl acetate and washed with 50 ml of water, after which it was dried over anhydrous magnesium sulfate. The mixture was filtered, and the solvent was removed from the filtrate by distillation under reduced pressure. The resulting residue was purified by silica gel column chromatography, using a 4:1 by volume mixture of hexane and ethyl acetate as the eluent, to give 70 mg (0.31 mmol) of the title compound (yield: 40% in two steps).

PREPARATION 11

1-(3-Chloropropionyl)-6-fluoroindoline

11(1) 1-(3-Chloropropionyl)indoline-6-diazonium tetrafluoroborate 1.12 g (5.0 mmol) of 6-amino-1-(3-chloropropionyl) indoline (prepared as described in Preparation 6) were suspended in 20 ml of 6N aqueous hydrochloric acid, and a solution of 380 mg (5.5 mmol) of sodium nitrite in 5 ml of water was added to the suspension while ice-cooling so that the internal temperature was maintained at 10° C. or lower. The mixture was then stirred while ice-cooling for 30 minutes. At the end of this time, 2.0 mg (8.4 mmol) of fluoboric acid (as a 42% w/v aqueous solution) were added to the mixture, and the resulting mixture was stirred at 0° C. for 1 hour. The precipitated salt was collected by filtration. This salt was dried over phosphorous pentoxide in a desiccator under reduced pressure by means of a vacuum pump overnight to obtain 1.23 g (3.8 mmol) of the title compound as a solid (yield: 76%).

11(2) 1-(3-Chloropropionyl)-6-fluoroindoline 1.23 g (3.8 mmol) of 1-(3-chloropropionyl)indoline-6-diazonium tetrafluoroborate [prepared as described in step (1) above] were suspended in 20 ml of heptane, and the suspension was heated under reflux for 1 hour. At the end of this time, the mixture was cooled to room temperature, and the reaction product was poured into ice. The mixture was then extracted with 50 ml of ethyl acetate, and the organic extract was washed with 50 ml of water, after which it was dried over anhydrous magnesium sulfate. The mixture was filtered, and then the solvent was removed from the filtrate by distillation under reduced pressure. The resulting residue was purified by silica gel column chromatography, using a 4:1 by volume mixture of hexane and ethyl acetate as the eluent, to give 810 mg (3.6 mmol) of the title compound (yield: 95%).

PREPARATION 12

1-(3-Chloropropionyl-6-fluoroindoline

12(1) 1-(3-Chloropropionyl)indoline-6-diazonium tetrafluoroborate 1.12 g (5.0 mmol) of 6-amino-1-(3-chloropropionyl) indoline (prepared as described in Preparation 6) were suspended in 10 ml of fluoboric acid (as a 42% w/v aqueous solution), and a solution of 380 mg (5.5 mmol) of sodium nitrite in 5 ml of water was added to the suspension while ice-cooling so that the internal temperature was maintained at 10° C. or lower. The mixture was then stirred while ice-cooling for 1 hour. The precipitated salt was collected by filtration and dried in a desiccator under reduced pressure by means of a vacuum pump to obtain 1.20 g (3.7 mmol) of the title compound as a solid (yield: 74%).

12(2) 1-(3-Chloropropyl)-6-fluoroindoline 1.20 g (3.7 mmol) of 1-(3-chloropropionyl)indoline-6-diazonium tetrafluoroborate [prepared as described in step (1) above] was suspended in 2 ml of heptane, and the suspension was heated under reflux for 2 hours. After the resulting mixture had cooled to room temperature, the reaction product was poured into ice, and the mixture was extracted with 50 ml of ethyl acetate. The organic extract was washed with 50 ml of water, after which it was dried over anhydrous magnesium sulfate. The mixture was then filtered, and the solvent was removed from the filtrate by distillation under reduced pressure. The resulting residue was purified by silica gel column chromatography, using a 4:1 by volume mixture of hexane and ethyl acetate as the eluent, to give 710 mg (3.1 mmol) of the title compound (yield: 84%).

FORMULATION 1

Wettable Powders

80% by weight of Compound No. 1, 2% of sodium alkylnaphthalenesulfonate, 2% of sodium ligninsulfonate, 3% of synthesized amorphous silica and 13% of kaolinite were mixed and pulverized by a hammer mill and the resulting mixture was again mixed and packaged.

FORMULATION 2

Wettable Powders

25% by weight of Compound No. 2, 2.5% of sodium dodecylbenzenesulfonate, 2.5% of sodium ligninsulfonate, 55% of diatomaceous earth and 15% of synthesized amorphous silica were mixed and pulverized to obtain a wettable powder.

FORMULATION 3

Emulsifiable Concentrates

15% by weight of Compound No. 1, 35% of cyclohexanone, 11% of polyoxyethylene nonylphenyl ether, 4% of calcium dodecylbenzenesulfonate and 35% of methylnaphthalene were homogeneously dissolved to obtain an emulsifiable concentrate.

FORMULATION 4

Emulsifiable Concentrates

15% by weight of Compound No. 39, 25% of a mixture of calcium dodecylbenzenesulfonate and a non-ionic surface active agent and 60% of xylene were combined and stirred to dissolve the active ingredient.

FORMULATION 5

Granules

5% by weight of Compound No. 1, 2% of sodium laurylsulfate, 5% of sodium ligninsulfonate, 2% of sodium carboxymethyl cellulose and 86% of clay were homogeneously mixed and pulverized. 20 parts by weight of water were added to 100 parts by weight of the mixture, and the resulting mixture was kneaded. The mixture was then processed to form a granular shape of 14–32 mesh (Tyler mesh standard) by means of an extrusion granulating machine and dried to obtain granules.

FORMULATION 6

Granules

5% by weight of Compound No. 2, 30% of bentonite, 62% of talc, 2% of sodium ligninsulfonate and 1% of sodium dodecylbenzenesulfonate were homogeneously mixed and pulverized. 20 parts by weight of water were added to 100 parts by weight of the mixture, and the resulting mixture was kneaded. The mixture was then processed to form a granular shape of 14–32 mesh (Tyler mesh standard) by means of an extrusion granulating machine and dried to obtain granules.

FORMULATION 7

Granules

4% by weight of Compound No. 39, 30% of bentonite, 63% of clay, 1% of polyvinyl alcohol and 2% of sodium dodecylbenzenesulfonate were homogeneously mixed and pulverized. 20 parts by weight of water were added to 100 parts by weight of the mixture, and the resulting mixture was kneaded. The mixture was then processed to form a granular shape of 14–32 mesh (Tyler mesh standard) by means of an extrusion granulating machine and dried to obtain granules.

FORMULATION 8
Granules

4% by weight of Compound No. 1, 35% of bentonite, 58.8% of talc, 2% of sodium alkylnaphthalenesulfonate and 0.2% of sodium dioctylsulfosuccinate were homogeneously mixed and pulverized. 20 parts by weight of water were added to 100 parts by weight of the mixture, and the resulting mixture was kneaded. The mixture was then processed to form a granular shape of 14–32 mesh (Tyler mesh standard) by means of an extrusion granulating machine and dried to obtain granules.

FORMULATION 9
Granules

5% by weight of Compound No. 39, 1% of white carbon, 5% of sodium ligninsulfonate, 84% of clay and 5% of sodium carboxymethyl cellulose were thoroughly pulverized and mixed. Water was then added to the mixture, which was then kneaded. The resulting mixture was granulated and dried to obtain granules.

FORMULATION 10
Dusts

2% by weight of Compound No. 1, 5% of diatomaceous earth and 93% of clay were homogeneously mixed and pulverized to obtain a dust.

FORMULATION 11
Soluble Liquids

30% by weight of Compound No. 1 and 70% of dimethyl sulfoxide were combined and stirred to obtain a soluble liquid.

FORMULATION 12
Granules 30 parts by weight of bentonite, 64.5 parts of talc and 0.5 part of sodium dioctylsulfosuccinate were homogeneously mixed. 18 parts of water were added to 95 parts of the mixture, and the resulting mixture was kneaded. The mixture was then granulated by means of an extrusion granulating machine, after which it was dried and sifted to obtain a granular carrier of 14–32 mesh (Tyler mesh standard). A solution obtained by dissolving 5 parts of Compound No. 39 in 20 parts of acetone was added to 95 parts of the granular carrier and was absorbed therein. It was then homogeneously mixed and air-dried to obtain granules.

FORMULATION 13
Granules 86 parts by weight of clay, 0.5 part of sodium dioctylsulfosuccinate, 7 parts of dextrin, 1.5 parts of sodium carboxymethyl cellulose were homogeneously mixed. 14 parts of water were added to 95 parts of the mixture, and the resulting mixture was kneaded. The mixture was then granulated by means of an extrusion granulating machine, after which it was dried and sifted to obtain a granular carrier of 14–32 mesh (Tyler mesh standard). A solution obtained by dissolving 5 parts of Compound No. 2 in 20 parts of acetone was added to 95 parts of the granular carrier and was absorbed therein. It was then homogeneously mixed and air-dried to obtain granules.

FORMULATION 14
Suspension Concentrates

30% by weight of Compound No. 1 was suspended in a solution obtained by dissolving 1% of sodium dodecylbenzenesulfonate and 5% of the condensation product of sodium naphthalenesulfonate with formaldehyde in 41.8% of water. The suspension was pulverized by means of a sand mill to make the average particle diameter 1.5 μm. Separately, a solution was prepared by dissolving and dispersing 0.2% of xanthan gum and 2% of magnesium aluminosilicate in 20% of water and was added to the above-mentioned pulverized slurry, followed by homogeneous stirring of the mixture to obtain a suspension concentrate.

FORMULATION 15
Emulsions in Water

5% by weight of Compound No. 1, 15% of xylene, 3.5% of polyoxyethylene nonylphenyl ether and 1.5% of calcium dodecylbenzenesulfonate were homogeneously mixed to prepare a solution. The solution was added to 41.65% of water while stirring, and a fine emulsion was prepared by means of a homogenizer. Separately, a liquid was prepared by dissolving and dispersing 0.35% of xanthan gum and 3% of magnesium aluminosilicate in 30% of water and this was combined with the above-mentioned emulsion and uniformly stirred to obtain an emulsion in water.

FORMULATION 16
Water Dispersible Granules

60% by weight of Compound No. 2, 15% of sodium ligninsulfonate, 17% of clay, 5% of granular calcium carbonate and 3% of sodium dodecylbenzene-sulfonate were mixed and pulverized by means of a jet mill. The pulverized product was placed in a fluidized bed granulation drying machine and granulated while spraying with water, after which it was dried and sifted through a 32–100 mesh (Tyler mesh standard) to obtain a granular wettable powder.

FORMULATION 17
Jumbo Formulations

These are formulations for throwing into a paddy field.

15.0 parts by weight of cork meal, 4.0 parts of the sodium salt of carboxymethyl cellulose, 41.0 parts of wood flour and 40.0 parts of bentonite were homogeneously mixed. Water was added to the mixture, and the resulting mixture was kneaded, and then granulated by means of an extrusion granulating machine. The granules were dried and adjusted to a size of 0.3 to 5 mm to obtain a granular carrier.

Separately, 24.0 parts of Compound No. 2, 3.0 parts of talc and 1.0 part of amorphous silicon dioxide were mixed and pulverized by means of a hammer mill to obtain a premix containing 85% of Compound No. 2.

10.0 parts of liquid paraffin were added to 73.4 parts of the above-mentioned granular carrier and the surface of the granules was wetted, after which 14.1 parts of the premix were added, and the whole was mixed to coat the mixture on the surface of the granules. 2.5 parts of Surfinol 104S (an acetylene type surface active agent, available from Nisshin Kagaku K.K.) were added to the granules and mixed, followed by coating to obtain granules containing 12% of Compound No. 2. 50 g of the resulting granules were each packed in a film of polyvinyl alcohol to obtain a jumbo formulation.

FORMULATION 18

Jumbo Formulations 24.0 parts by weight of Compound No. 1, 3.0 parts of talc and 1.0 part of amorphous silicon dioxide were mixed and pulverized by means of a hammer mill to obtain a premix containing 85% of Compound No. 1.

35 parts of liquid paraffin were mixed with 35 parts of calcined vermiculite to wet the surface of the vermiculite. 28 parts of the above-mentioned premix were added in four portions to the coated vermiculite, followed by mixing, to coat the premix on the surface of the granules. Then 2 parts of Surfinol 104S (an acetylene type surface active agent, available from Nisshin Kagaku K.K.) were added to the granules, followed by further mixing and coating to obtain granules containing 12% of Compound No. 1. 50 g of the resulting granules were each packed in a film of polyvinyl alcohol to obtain a jumbo formulation.

We claim:

1. A compound of formula (I):

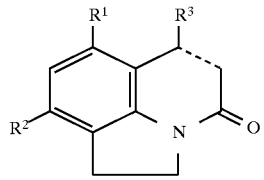

wherein:
R¹ represents
a halogen atom,
an alkyl group having from 1 to 6 carbon atoms,
a haloalkyl group having from 1 to 6 carbon atoms,
an alkoxy group having from 1 to 6 carbon atoms,
a haloalkoxy group having from 1 to 6 carbon atoms,
a cycloalkyl group having from 3 to 7 carbon atoms, or
a cycloalkyloxy group having from 3 to 7 carbon atoms;
$R^2$ represents a hydrogen atom or a halogen atom;
$R^3$ represents
a hydrogen atom,
an alkyl group having from 1 to 6 carbon atoms, or
a cycloalkyl group having from 3 to 7 carbon atoms; and
the dotted line represents a single or double carbon—carbon bond;
and salts thereof.

2. The compound of claim 1, wherein $R^1$ represents a fluorine atom, a chlorine atom, a bromine atom, an alkyl group having from 1 to 6 carbon atoms, a haloalkyl group having from 1 to 6 carbon atoms and having from 1 to 3 halogen atoms which may be the same as or different from each other, an alkoxy group having from 1 to 6 carbon atoms or a haloalkoxy group having from 1 to 6 carbon atoms and having from 1 to 3 halogen atoms which may be the same as or different from each other.

3. The compound of claim 1, wherein $R^1$ represents a fluorine atom, a chlorine atom, a methyl group, a methoxy group, a difluoromethoxy group or a trifluoromethoxy group.

4. The compound of claim 1, wherein $R^1$ represents a fluorine atom, a chlorine atom, a methyl group or a difluoromethoxy group.

5. The compound of claim 1, wherein $R^1$ represents a fluorine atom, a chlorine atom or a difluoromethoxy group.

6. The compound of claim 1, wherein $R^1$ represents a fluorine atom or a chlorine atom.

7. The compound of claim 1, wherein $R^2$ represents a hydrogen atom, a fluorine atom, a chlorine atom or a bromine atom.

8. The compound of claim 1, wherein $R^2$ represents a hydrogen atom, a fluorine atom or a chlorine atom.

9. The compound of claim 1, wherein $R^2$ represents a hydrogen atom, a fluorine atom, a chlorine atom.

10. The compound of claim 1, wherein $R^2$ represents a hydrogen atom or a fluorine atom.

11. The compound of claim 1, wherein $R^2$ represents a hydrogen atom.

12. The compound of claim 1, wherein $R^3$ represents a hydrogen atom or an alkyl group having from 1 to 4 carbon atoms.

13. The compound of claim 1, wherein $R^3$ represents a hydrogen atom, a methyl group or an ethyl group.

14. The compound of claim 1, wherein $R^3$ represents a hydrogen atom.

15. The compound of claim 1, wherein $R^3$ represents a methyl group.

16. The compound of claim 1, wherein the dotted line represents a single bond.

17. The compound of claim 1, wherein the dotted line represents a double bond.

18. The compound of claim 1, wherein:
$R^1$ represents a fluorine atom, a chlorine atom, a bromine atom, an alkyl group having from 1 to 6 carbon atoms, a haloalkyl group having from 1 to 6 carbon atoms and having from 1 to 3 halogen atoms which may be the same as or different from each other, an alkoxy group having from 1 to 6 carbon atoms or a haloalkoxy group having from 1 to 6 carbon atoms and having from 1 to 3 halogen atoms which may be the same as or different from each other; and
$R^3$ represents a hydrogen atom or an alkyl group having from 1 to 4 carbon atoms.

19. The compound of claim 1, wherein:
$R^1$ represents a fluorine atom, a chlorine atom, a methyl group, a methoxy group, a difluoromethoxy group or a trifluoromethoxy group;
$R^2$ represents a hydrogen atom, a fluorine atom, a chlorine atom or a bromine atom; and
$R^3$ represents a hydrogen atom, a methyl group or an ethyl group.

20. The compound of claim 1, wherein:
$R^1$ represents a fluorine atom, a chlorine atom, a methyl group or a difluoromethoxy group;
$R^2$ represents a hydrogen atom, a fluorine atom or a chlorine atom;
$R^3$ represents a hydrogen atom; and
the dotted line represents a single bond.

21. The compound of claim 1, wherein:
$R^1$ represents a fluorine atom, a chlorine atom, a methyl group or a difluoromethoxy group;
$R^2$ represents a hydrogen atom, a fluorine atom, a chlorine atom;
$R^3$ represents a methyl group; and
the dotted line represents a double bond.

22. The compound of claim 1, wherein:
$R^1$ represents a fluorine atom, a chlorine atom or a difluoromethoxy group;
$R^2$ represents a hydrogen atom or a fluorine atom;
$R^3$ represents a hydrogen atom; and
the dotted line represents a single bond.

23. The compound of claim 1, wherein:
$R^1$ represents a fluorine atom or a chlorine atom;
$R^2$ represents a hydrogen atom;

$R^3$ represents a hydrogen atom; and
the dotted line represents a single bond.

24. The compound of claim 1, selected from the group consisting of 7-fluoro-1,2,5,6-tetrahydro-4H-pyrrolo[3,2,1-ij]quinolin-4-one and salts thereof.

25. The compound of claim 1, selected from the group consisting of 7-chloro-1,2,5,6-tetrahydro-4H-pyrrolo[3,2,1-ij]quinolin-4-one and salts thereof.

26. The compound of claim 1, selected from the group consisting of 7,9-difluoro-1,2,5,6-tetrahydro-4H-pyrrolo[3,2,1-ij]quinolin-4-one and salts thereof.

27. The compound of claim 1, selected from the group consisting of 7-difluoromethoxy-6-methyl-1,2-dihydro-4H-pyrrolo[3,2,1-ij]quinolin-4-one and salts thereof.

28. A process for preparing a compound of formula (If):

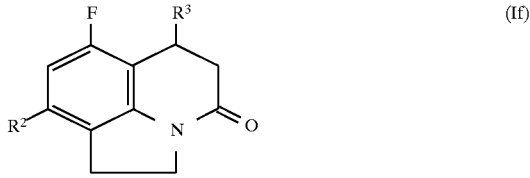

wherein:
$R^2$ represents a hydrogen atom or a halogen atom; and
$R^3$ represents
a hydrogen atom,
an alkyl group having from 1 to 6 carbon atoms, or
a cycloalkyl group having from 3 to 7 carbon atoms;
which comprises the steps:
diazotising a compound of formula (V):

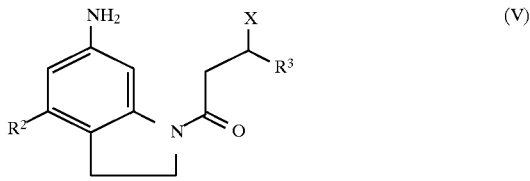

wherein X represents a chlorine or bromine atom and $R^2$ and $R^3$ are as defined above, in the presence of a fluorine-containing compound capable of generating a fluorine anion, and heating the product to give a compound of formula (VI):

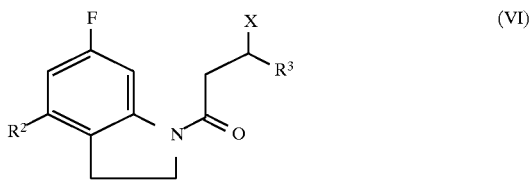

wherein X, $R^2$ and $R^3$ are as defined above, and then ring-closing said compound of formula (VI) to give said compound of formula (If).

29. The process of claim 28, wherein the diazotisation is effected in the presence of a hydrofluoric acid.

30. The process of claim 29, wherein said hydrofluoric acid is fluoboric acid, hexafluorophosphoric acid, hexafluoroarsenic acid, fluoroantimonic acid or hydrofluoric acid.

31. The process of claim 28, wherein the diazotisation is effected in the presence of a tetrafluoroborate.

32. The process of claim 31, wherein said tetrafluoroborate is sodium tetrafluoroborate, ammonium tetrafluoroborate or potassium tetrafluoroborate.

33. A method of protecting plants from fungal infection by applying to said plants, to reproductive matter of said plants or to a locus including said plants an effective amount of at least one active compound of formula (I) or a salt thereof, as claimed in claim 1.

34. The method of claim 33, wherein:
$R^1$ represents a fluorine atom, a chlorine atom, a bromine atom, an alkyl group having from 1 to 6 carbon atoms, a haloalkyl group having from 1 to 6 carbon atoms and having from 1 to 3 halogen atoms which may be the same as or different from each other, an alkoxy group having from 1 to 6 carbon atoms or a haloalkoxy group having from 1 to 6 carbon atoms and having from 1 to 3 halogen atoms which may be the same as or different from each other; and
$R^3$ represents a hydrogen atom or an alkyl group having from 1 to 4 carbon atoms.

35. The method of claim 33, wherein:
$R^1$ represents a fluorine atom, a chlorine atom, a methyl group, a methoxy group, a difluoromethoxy group or a trifluoromethoxy group;
$R^2$ represents a hydrogen atom, a fluorine atom, a chlorine atom or a bromine atom; and
$R^3$ represents a hydrogen atom, a methyl group or an ethyl group.

36. The method of claim 33, wherein:
$R^1$ represents a fluorine atom, a chlorine atom, a methyl group or a difluoromethoxy group;
$R^2$ represents a hydrogen atom, a fluorine atom or a chlorine atom;
$R^3$ represents a hydrogen atom; and
the dotted line represents a single bond.

37. The method of claim 33, wherein:
$R^1$ represents a fluorine atom, a chlorine atom, a methyl group or a difluoromethoxy group;
$R^2$ represents a hydrogen atom, a fluorine atom, a chlorine atom;
$R^3$ represents a methyl group; and
the dotted line represents a double bond.

38. The method of claim 33, wherein:
$R^1$ represents a fluorine atom, a chlorine atom or a difluoromethoxy group;
$R^2$ represents a hydrogen atom or a fluorine atom;
$R^3$ represents a hydrogen atom; and
the dotted line represents a single bond.

39. The method of claim 33, wherein:
$R^1$ represents a fluorine atom or a chlorine atom;
$R^2$ represents a hydrogen atom;
$R^3$ represents a hydrogen atom; and
the dotted line represents a single bond.

40. The method of claim 33, wherein said active compound is selected from the group consisting of:
7-fluoro-1,2,5,6-tetrahydro-4H-pyrrolo[3,2,1-ij]quinolin-4-one;
7-chloro-1,2,5,6-tetrahydro-4H-pyrrolo[3,2,1-ij]quinolin-4-one;
7,9-difluoro-1,2,5,6-tetrahydro-4H-pyrrolo[3,2,1-ij]quinolin-4-one; and
7-difluoromethoxy-6-methyl-1,2-dihydro-4H-pyrrolo[3,2,1-ij]quinolin-4-one;
and salts thereof.

41. A method of treating fungal infection in a plant applying to said plant or to a locus including said plant an effective amount of at least one active compound of formula (I) or a salt thereof, as claimed in claim 1.

42. The method of claim 41, wherein:

$R^1$ represents a fluorine atom, a chlorine atom, a bromine atom, an alkyl group having from 1 to 6 carbon atoms, a haloalkyl group having from 1 to 6 carbon atoms and having from 1 to 3 halogen atoms which may be the same as or different from each other, an alkoxy group having from 1 to 6 carbon atoms or a haloalkoxy group having from 1 to 6 carbon atoms and having from 1 to 3 halogen atoms which may be the same as or different from each other; and $R^3$ represents a hydrogen atom or an alkyl group having from 1 to 4 carbon atoms.

43. The method of claim 41, wherein:

$R^1$ represents a fluorine atom, a chlorine atom, a methyl group, a methoxy group, a difluoromethoxy group or a trifluoromethoxy group;

$R^2$ represents a hydrogen atom, a fluorine atom, a chlorine atom or a bromine atom; and $R^3$ represents a hydrogen atom, a methyl group or an ethyl group.

44. The method of claim 41, wherein:

$R^1$ represents a fluorine atom, a chlorine atom, a methyl group or a difluoromethoxy group;

$R^2$ represents a hydrogen atom, a fluorine atom or a chlorine atom;

$R^3$ represents a hydrogen atom; and
the dotted line represents a single bond.

45. The method of claim 41, wherein:

$R^1$ represents a fluorine atom, a chlorine atom, a methyl group or a difluoromethoxy group;

$R^2$ represents a hydrogen atom, a fluorine atom, a chlorine atom;

$R^3$ represents a methyl group; and
the dotted line represents a double bond.

46. The method of claim 41, wherein:

$R^1$ represents a fluorine atom, a chlorine atom or a difluoromethoxy group;

$R^2$ represents a hydrogen atom or a fluorine atom;

$R^3$ represents a hydrogen atom; and
the dotted line represents a single bond.

47. The method of claim 41, wherein:

$R^1$ represents a fluorine atom or a chlorine atom;

$R^2$ represents a hydrogen atom;

$R^3$ represents a hydrogen atom; and
the dotted line represents a single bond.

48. The method of claim 41, wherein said active compound is selected from the group consisting of:

7-fluoro-1,2,5,6-tetrahydro-4H-pyrrolo[3,2,1-i,j]quinolin-4-one;

7-chloro-1,2,5,6-tetrahydro-4H-pyrrolo[3,2,1-ij]quinolin-4-one;

7,9-difluoro-1,2,5,6-tetrahydro 4H-pyrrolo[3,2,1-ij]quinolin-4-one; and 7-difluoromethoxy-6-methyl-1,2-dihydro-4H-pyrrolo[3,2,1-ij]quinolin-4-one;

and salts thereof.

* * * * *